(12) United States Patent
Brown et al.

(10) Patent No.: US 10,927,144 B2
(45) Date of Patent: Feb. 23, 2021

(54) METHODS FOR REMOVING A CONTAMINANT USING INDIGENOUS PROTEIN DISPLACEMENT ION EXCHANGE MEMBRANE CHROMATOGRAPHY

(75) Inventors: Arick Brown, Pacifica, CA (US); Jerome Bill, Jr., San Francisco, CA (US); Timothy Tully, San Francisco, CA (US); Christopher Dowd, Belmont, CA (US)

(73) Assignee: GENENTECH, INC., South San Francisco, CA (US)

( * ) Notice: Subject to any disclaimer, the term of this patent is extended or adjusted under 35 U.S.C. 154(b) by 284 days.

(21) Appl. No.: 13/058,796

(22) PCT Filed: Aug. 14, 2008

(86) PCT No.: PCT/US2008/073179
§ 371 (c)(1),
(2), (4) Date: May 4, 2011

(87) PCT Pub. No.: WO2010/019148
PCT Pub. Date: Feb. 18, 2010

(65) Prior Publication Data
US 2012/0122759 A1 May 17, 2012

(51) Int. Cl.
 C07K 1/18 (2006.01)
 C07K 1/34 (2006.01)
 C07K 1/36 (2006.01)
(52) U.S. Cl.
 CPC ............... *C07K 1/18* (2013.01); *C07K 1/34* (2013.01); *C07K 1/36* (2013.01)
(58) Field of Classification Search
 None
 See application file for complete search history.

(56) References Cited

U.S. PATENT DOCUMENTS

| | | |
|---|---|---|
| RE30,985 E | 6/1982 | Cartaya |
| 4,347,322 A | 8/1982 | Johnson et al. |
| 4,515,893 A | 5/1985 | Kung et al. |
| 4,560,655 A | 12/1985 | Baker |
| 4,657,866 A | 4/1987 | Kumar |
| 4,767,704 A | 8/1988 | Cleveland et al. |
| 4,816,567 A | 3/1989 | Cabilly et al. |
| 4,927,762 A | 5/1990 | Darfler |
| 5,091,178 A | 2/1992 | Hellstrom et al. |
| 5,122,469 A | 6/1992 | Mather et al. |
| 5,534,615 A | 7/1996 | Baker et al. |
| 5,595,721 A | 1/1997 | Kaminski et al. |
| 5,622,700 A | 4/1997 | Jardieu et al. |
| 5,677,180 A | 10/1997 | Robinson et al. |
| 5,693,762 A | 12/1997 | Queen et al. |
| 5,714,338 A | 2/1998 | Wai Fei et al. |
| 5,725,856 A | 3/1998 | Hudziak et al. |
| 5,736,137 A | 4/1998 | Anderson et al. |
| 7,323,553 B2 | 1/2008 | Fahrner et al. |
| 8,420,789 B2 | 4/2013 | Takeda et al. |
| 2002/0187206 A1 | 12/2002 | Mirkov et al. |
| 2003/0219433 A1 | 11/2003 | Hansen et al. |
| 2003/0229212 A1* | 12/2003 | Fahrner et al. ............... 530/417 |
| 2004/0093621 A1 | 5/2004 | Shitara et al. |
| 2004/0167319 A1 | 8/2004 | Teeling et al. |
| 2005/0025764 A1 | 2/2005 | Watkins et al. |
| 2005/0069545 A1 | 3/2005 | Carr et al. |
| 2006/0142549 A1* | 6/2006 | Takeda et al. ............... 530/351 |

FOREIGN PATENT DOCUMENTS

| | | |
|---|---|---|
| EP | 183070 | 6/1986 |
| EP | 244234 | 11/1987 |
| EP | 402226 | 12/1990 |
| EP | 0420937 | 11/1994 |
| EP | 404097 | 9/1996 |
| EP | 2 321 337 A1 | 5/2011 |
| EP | 2 321 337 B1 | 5/2011 |
| EP | 2 321 337 B9 | 5/2011 |
| KR | 10-2006-0081422 | 7/2006 |
| KR | 1020070107753 A | 11/2007 |
| WO | WO 1987/00195 | 1/1987 |
| WO | WO 1990/03430 | 4/1990 |
| WO | WO 1993/11161 | 6/1993 |
| WO | WO 1993/16185 | 8/1993 |
| WO | WO 1995/008574 A1 | 3/1995 |
| WO | WO-1997/27757 A1 | 8/1997 |

(Continued)

OTHER PUBLICATIONS

Knudsen et al. (2001) J. of Chromatography A, 907, 145-154.*
Langlotz et al. "Surface-modified membranes as a matrix for protein purification", J. Chromatography 591:107-113, 1992.
Zhou et al. "Basic concepts in Q membrane chromatography for large-scale antibody production", Biotechnol. P 22:341-349, 2006.
Barnes et al. "Methods for growth of cultured cells in serum-free medium", Analytical Biochemistry 102:255-270, 1980.
Brennan et al. "Preparation of bispecific antibodies by chemical recombination of monoclonal immunoglobulin G; fragments", Science 229:81-83, 1985.
Bruggermann et al. "Designer mice: the production of human antibody repertoires in transgenic animals", Year Immunol. 7:33-40, 1993.
Carter et al. "High level *Escherichia coli* expression and production of a bivalent humanized antibody fragment", Bio/Technology 10:163-167, 1992.

(Continued)

*Primary Examiner* — Maury A Audet
(74) *Attorney, Agent, or Firm* — Morrison & Foerster LLP

(57) ABSTRACT

Methods for purifying a polypeptide from a composition comprising the polypeptide and at least one contaminant are described, which methods comprise the sequential steps of: (a) passing the composition through an ion exchange membrane, where the polypeptide and the membrane have opposite charge, at operating conditions comprised of a buffer having a pH sufficiently distinct from the pI of the polypeptide to enhance the charge of the polypeptide and a low ionic strength effective to prevent the shielding of charges by buffer ions, which cause the membrane to bind the polypeptide and the at least one contaminant, and (b) recovering the purified polypeptide from the effluent.

29 Claims, 8 Drawing Sheets

(56) References Cited

FOREIGN PATENT DOCUMENTS

| WO | WO 1998/23761 | 6/1998 |
|---|---|---|
| WO | WO 1998/45331 | 10/1998 |
| WO | WO 2002/24909 | 3/2002 |
| WO | WO 02/068452 | 9/2002 |
| WO | WO-2002/06845 A2 | 9/2002 |
| WO | WO-2002/068452 A3 | 9/2002 |
| WO | WO 2004/103404 | 12/2004 |
| WO | WO 2005/16969 | 2/2005 |
| WO | 2006086586 A2 | 8/2006 |
| WO | WO 2006/099308 A2 | 9/2006 |
| WO | 2006086586 A3 | 10/2006 |
| WO | WO 2007/108955 A1 | 9/2007 |
| WO | WO 2005/044856 A2 | 5/2008 |
| WO | WO 2008/057683 | 5/2008 |
| WO | WO-2009/135656 A1 | 11/2009 |

OTHER PUBLICATIONS

Carter et al. "Humanization of an anti-p185$^{HER2}$ antibody for human cancer therapy", Proc. Natl. Acad, Sci. USA, 89:4285-4289, 1992.
Ceriani et al. "Biological activity of two humanized antibodies against two different breast cancer antigens and comparison to their original murine forms", Cancer Research 55:5852s-5856s, 1995.
Chothia et al. "Canonical structures for the hypervariable regions of immunolobulins", J. Mol. Biol. 196:901-917, 1987.
Choy et al. "Percentage of anti-CD4 monoclonal antibody-coated lymphocytes in the rheumatoid joint is associated with clinical improvement", Arthritis & Rheumatism 39(1):52-56, 1996.
Clackson et al. "Making antibody fragment using phage display libraries", Nature 352:624-628, 1991.
Cragg et al. "Complement-mediated lysis by anti-CD20 mAb correlates with segregation into lipid rafts", Blood 101:1045-1052, 2003.
Duchosal et al. "Immunization of hu-PBL-SCID mice and the rescue of human monoclonal Fab fragments through combinatorial libraries", Nature 355:258-262,1992.
Ellis et al. "Engineered anti-CD38 monoclonal antibodies for immunotherapy of multiple myeloma", J. Immunol, 155(2):925-937,1995.
Glennie et al. "Renaissance of cancer therapeutic", Drug Discovery Today 8:503-510, 2003.
Graham et al. "Characteristics of a human cell line transformed by DNA from human adenovirus Type 5", J. Gen Virol, 36:59-72, 1977.
Graziano et al. "Construction and characterization of a humanized anti-γ1g receptor type I (FcγRI) monoclonal antibody", J. Immunol. 155(10):4996-5002, 1995.
Haisma et al. "Construction and characterization of a fusion protein of single-chain anti-CD2O antibody and human β-Glucuronidase for antibody-directed enzyme prodrug therapy", Blood 92:184-190,1998.
Ham et al. "Media and growth requirements", Methods Enzymology LVIII:44-92,1979.
Holliger et al. "Diabodies: Small bivalent and bispecific antibody fragments", Proc. Natl. Acad. Sci. USA 90:6444-6448, 1993.
Hourmant et al. "Administration of an anti-CD11a monoclonal antibody in recipients of kidney transplantation", Transplantation 58(3):377-380, 1994.
Jakobovits et al. "Analysis of homozygous mutant chimeric mice: Deletion of the immunoglobulin heavy-chain joining region blocks B-cell development and antibody production", Proc. Natl. Acad. Sci. USA 90:2551-2555, 1993.
Jakobovits et al. "Germ-line transmission and expression of a human-derived yeast artificial chromosome", Nature 362:255-258, 1993.
Jurcic et al. "Radiolabeled anti-CD33 monoclonal antibody M195 for Myeloid leukemias$^{a}$", Cancer Research 55:5908s-5910s, 1995.

Kim et al. "The vascular endothelial growth factor proteins: Identification of biologically relevant regions by neutralizing monoclonal antibodies", Growth Factors 7:53-64,1992.
Kohler et al. "Continuous cultures of fused cells secreting antibody of predefined specificty", Nature 256:495-497, 1975.
Marks et al. "By-passing immunization human antibodies from V-gene libraries displayed on phage", J. Mol. Biol. 222:581-597,1991.
Marks et al. "By-passing immunization: Building high affinity human anibodies by chain shuffling", Bio/Technology 10:779-783, 1992.
Mather, J. "Establishment and characterization of two distinct mouse testicular epithelial cell lines", Biology Reproduction 23:243-252, 1980.
Mather er al. "Culture of testicular cells in hormones-supplemented serum-free medium" Annals N.Y. Academy of Science 383:44-68, 1982.
McCafferty et al. "Phage antibodies: filamentous page displaying antibody variable domains", Nature, 348:552-554, 1990.
Morrison et al. "Chimeric human antibody molecules: mouse antigen-binding domains with human constant region domains", Proc. Natl. Acad. Sci. USA 81:6851-6855, 1984.
Morimoto et al. "Single-step purification of F(ab')$_2$ fragments of mouse monoclonal antibodies (immunoglobulins G1) by hydrophobic interaction high performance liquid chromatography using TSKgel Phenyl-5PW", J. Biochemical and Biophysical Methods 24:107-117,1992.
Presta et al. "Humanization of an antibody directed against IgE", J. Immunol. I51:2623-2632, 1993.
Press et al. "Monoclonal antibody 1F5 (Anti-CD20) serotherapy of human B cell lymphomas", Blood 69(2):584-591,1987.
Richman et al. "Radioimmunotherapy for breast cancer using escalating fractionated doses of $^{131}$I-labeled chimeric L6 antibody with peripheral blood progenitor cell transfusions", Cancer Research 55: 5916s-5920s, 1995.
Riechmann et al. "Reshaping human antibodies for therapy", Nature 332:323-337, 1988.
Sharkey et al. "Evaluation of a complementary-determining region-grafter (humanized) anti-carcinoembryonic antigen monoclonal antibody in preclinical and clinical studies", Cancer Research 55:5935s-5945s, 1995.
Sims et al. "A humanized CD18 antibody can block function without cell destruction", J. Immunol., 151(4): 2296-2308, 1993.
Stoppa et al. "Anti-LFA1 monoclonal antibody (25.3) for treatmen of steriod-resistant grade III-IV actue graft-versus-host-disease", Transplant International 4:3-7,1991.
St John et al. "Immunologic therapy for ARDS, septic shock, and multiple-organ failure", Chest 103:932-943, 1993.
Tutt et al. "Trispecific F(ab')$_3$ derivatives that use cooperative signaling via the TCR/CD3 complex and CD2 to activate and redirect resting cytotoxic T cells", J. Immunol. 147: 60-69, 1991.
Urlaub et al. "Isolation of Chinese hamster cell mutants deficient in dihydrofolate reductase activity", Proc. Natl. Acad. Sci. USA 77(7):4216-4220, 1980.
Valentine et al. "Structure and function of the B-cell specific 35-37 kDa CD20 protein", B-cell Antigens B3.9:440-443, 1987.
Waterhouse et al. "Combinatorial infection and in vivo recombination a strategy for making large phase antibody repertoires", Nucleic Acids. Research 21(9); 2265-2266,1993.
Zapata et al. "Engineering linear F(ab')$_2$ fragments for efficient production in *Escherichia coli* and enhanced antiproliferative activity", Protein Engineering 8(10):1057-1062, 1995.
Avramescu et al. "Mixed-matrix membrane adsorbers for protein separation", J. Chromatography A. 1006:171-183, 2003.
Facts and Arguments by Novo Nordisk A/S in Opposition of European Patent No. EP 2 321 337 dated Jul. 22, 2015 (23 pages).
Fahrner, et. al., "Industrial purification of pharmaceutical antibodies: development, operation, and validation of chromatography of processes", Biotechnol. Genet. Eng. Rev., 2001, vol. 18, pp. 301-327.
Follman, et al., "Factorial screening of antibody purification processes using three chromatography steps without protein A," J Chromatogr A. Jan. 23, 2004;1024(1-2):79-85.

(56) References Cited

OTHER PUBLICATIONS

Frau, et al., "Scaling up disposable membrane chromatography," BioPharm International, Nov. 9, 2006, http://www.biopharminternational.com/scaling-disposable-membrane-chromatography (4 pgs).

Brown, et al., "Overloading ion-exchange membranes as a purification step for monoclonal antibodies," Biotechnol. Appl. Biochem., 2010, vol. 56, pp. 59-70.

Facts and Arguments by Baxalta GmbH in Opposition of European Patent No. EP 2 321 337 dated Jul. 22, 2015 (29 pages).

Facts and Arguments by Novo Nordisk A/S in Opposition of European Patent No. EP 2 321 337 dated Jul. 22, 2015 (21 pages).

Ghosh, Raja, "Protein separation using membrane chromatography: opportunities and challenges," Journal of Chromatography, 2002, vol. 952, pp. 13-27.

Goodall, et. al., "Selective Separation of the Major Whey Proteins Using Ino Exchange Membranes," J. Dairy Sci., 2008, vol. 91, pp. 1-10.

Gottschalk, et. al., "Bioseperation in Antibody Manufacturing: The Good, The Bad and The Ugly," Biotechnol. Prog., 2008, vol. 24, pp. 496-503.

Gottschalk, et. al., "Membrane Absorbers: A Cutting Edge Process Technology at the Threshold," Bioprocess Technical, May 2004, pp. 56-64.

Ion Exchange Chorography, Principals and Methods, Ch. 2, "Ion exchange chromatography," Pharmacia, 3rd Edition, pp. 6-7.

Knudsen, et. al., Membrane ion-exchange chromatography for process-scale antibody purification, 2001, vol. 907, pp. 145-154.

Mora, Jeff, "Scaling up Disposable Membrane Chromatography," Biopharminternational.com. 2008, retrieved from http://www.biopharminternational.com/scaling-disposable-membrane-chromatography on Jul. 14, 2015 (5 pages).

Notice of Opposition by Baxalta GmbH in Opposition of European Patent No. EP 2 321 337 dated Jul. 22, 2015 (4 pages).

Notice of Opposition by Novo Nordisk A/S in Opposition of European Patent No. EP 2 321 337 dated Jul. 22, 2015 (5 pages).

Pall Life Sciences, Application Note, "Contaminant Removal by Mustang® Q Membrane Chromatography from a Protein a Purified Monoclonal Antibody," 2007, pp. 1-3.

Thömmes, et. al., "Alternative to Chromatographic Separations," Biotechnol. Prog., 2007, vol. 23, pp. 42-45.

Veeraragavan, et. al., "Sample displacement mode chromatography: purification of proteins by use of a high-performance anion-exchange column," J. Chromat., 1991, vol. 541, pp. 207-220.

Amended Main Request claim set, dated Nov. 28, 2017 (3 pages).

Brief Communication-Opposition Proceedings, dated Nov. 3, 2017 (11 pages).

Letter regarding the opposition procedure, dated Dec. 23, 2016 (21 pages).

Main Request claim set, dated Jun. 2, 2016 (22 pages).

Observations by third parties, dated May 3, 2017 (12 pages).

Orr, et al., "Recent advances in bioprocessing application of membrane chromatography," Biotechnology Advances, 2013, 31, 450-465.

Reply of the patent proprietor to the notice of opposition, dated Jun. 2, 2016 (3 pages).

Result of Oral Proceedings, dated Nov. 2017 (8 pages).

Summons to Attend Oral Proceedings, Opinion of Opposition Division, dated Mar. 2, 2017 (11 pages).

European Opposition for European Patent No. EP08797895.3, dated Jan. 23, 2018, 60 pages.

European Opposition for European Patent No. EP08797895.3, dated Jun. 2, 2016, 58 pages.

Drager, F.E. "Application of the Stoichiometric Displacement Model of Retention to Anion-Exchange Chromatography of Nucleic Acids," J. Chromatorgr. 359:147-155, (1986).

International Preliminary Report on Patentability, dated Feb. 15, 2011, for PCT Application No. PCT/US2008/073179, filed Aug. 14, 20008, 5 pages.

International Search Report, dated Jun. 9, 2009 for PCT Application No. PCT/US208/073179, 2 pages.

Written Opinion of the International Searching Authority, dated Jun. 9, 2009, for PCT Application No. PCT/US2008/073179, filed Aug. 14, 20008, 4 pages.

Fahrner et al., "Industrial purification of pharmaceutical antibodies: development, operation, and validation of chromatography processes."Biotechnol Genet Eng Rev. 2001; 18: 301-327.

Drager, F.E. Regnier,"Application of the stoichiometric displacement model of retention to anion-exchange chromatography of nucleic acids,". J Chromatogr. 359:147-55 (1986).

International Search Report dated Jun. 9, 2009 for related PCT Patent Application No. PCT/US2008/073179.

\* cited by examiner

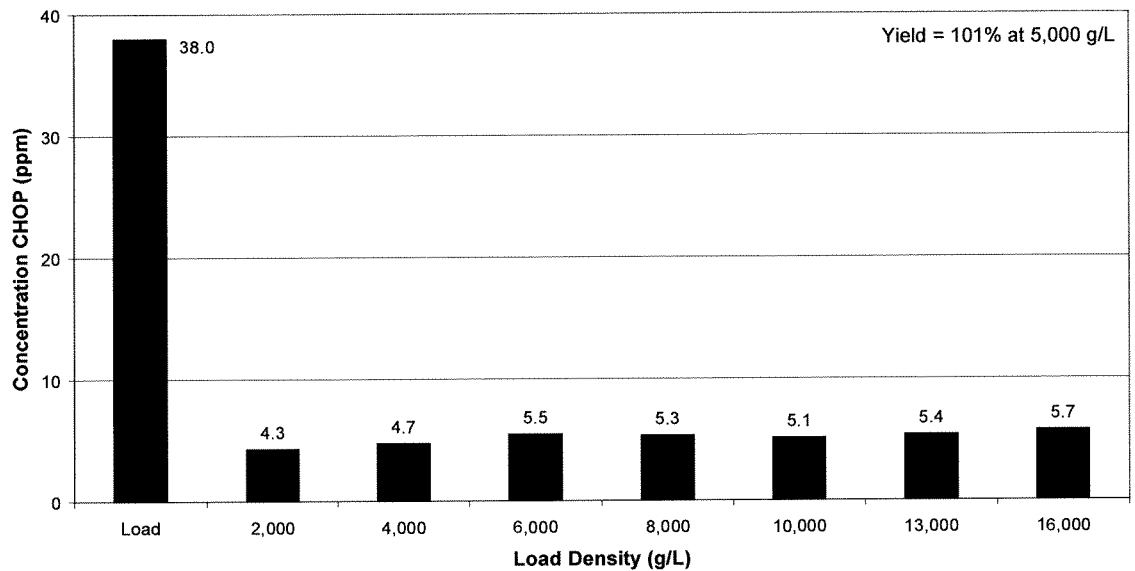
Figure 1: CHOP clearance for mAb 1 anion exchange pool at pH 5.5, 6.0 mS/cm, Mustang™ S (Small-scale, 0.18 mL MV, 667 MV/hour).
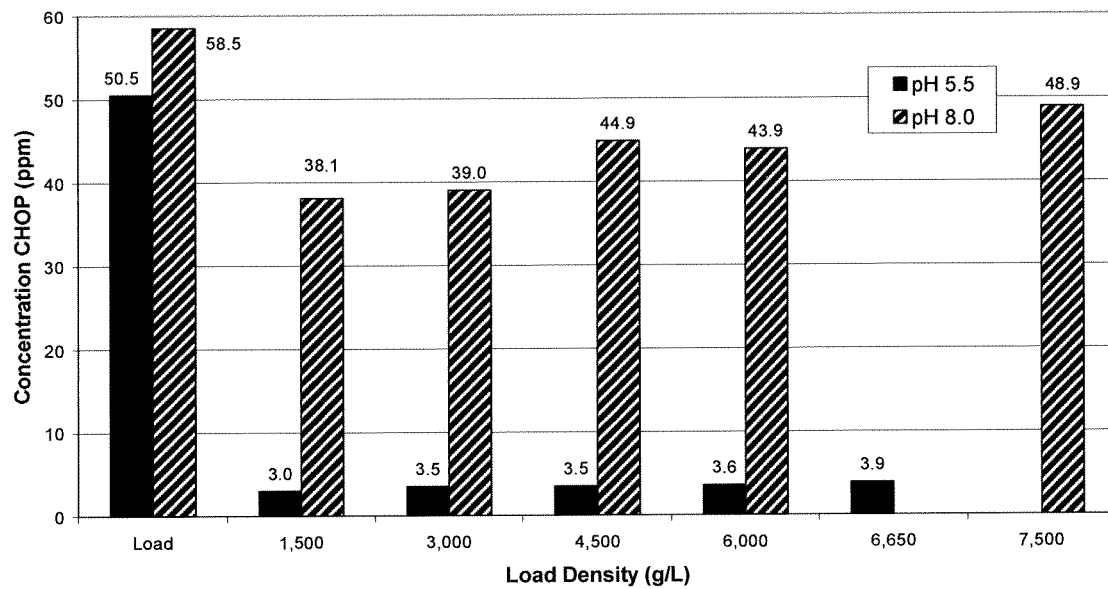
Figure 2: CHOP clearance for mAb 2 anion exchange pool at pH 5.5 and 6.4 mS/cm and at pH 8.0 and 5.0 mS/cm, Mustang™ S (Small-scale, 0.18 mL MV, 667 MV/hour).

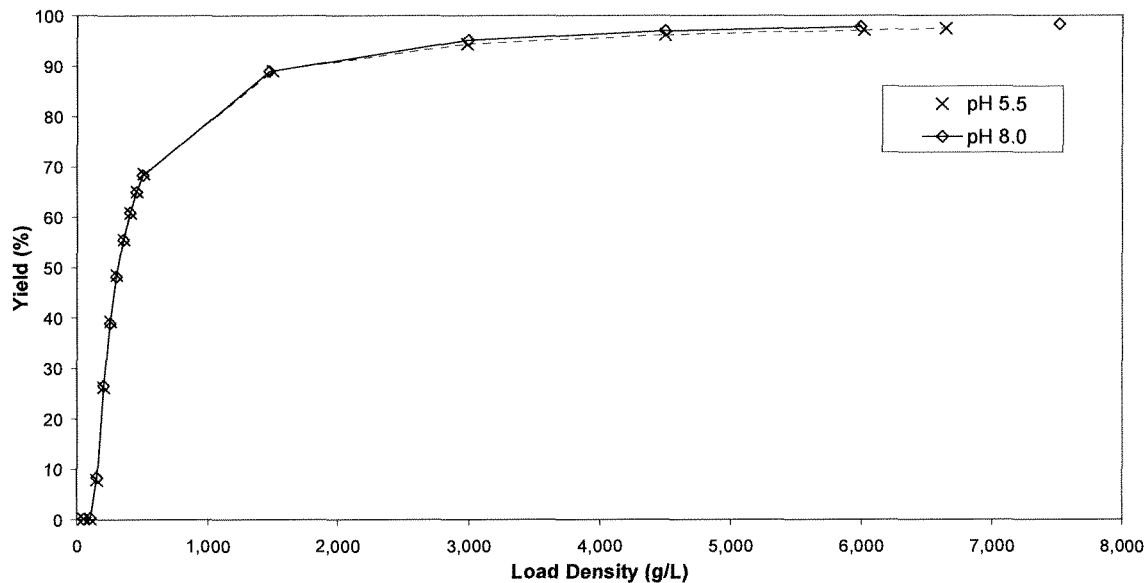
Figure 3: Yield for mAb 2 anion exchange pool at pH 5.5 and 6.4 mS/cm and at pH 8.0 and 5.0 mS/cm, Mustang™ S (Small-scale, 0.18 mL MV, 667 MV/hour).
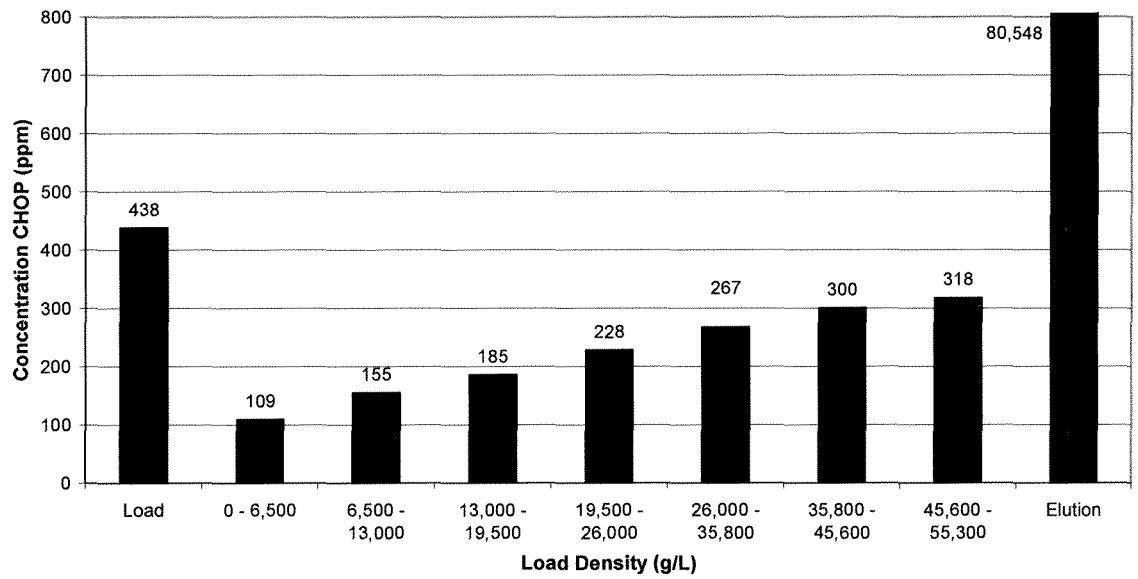
Figure 4: CHOP clearance for mAb 1 Protein A pool at pH 5.5, 3.2 mS/cm, Mustang™ S (Small-scale, 0.18 mL MV, 1333 MV/hour).

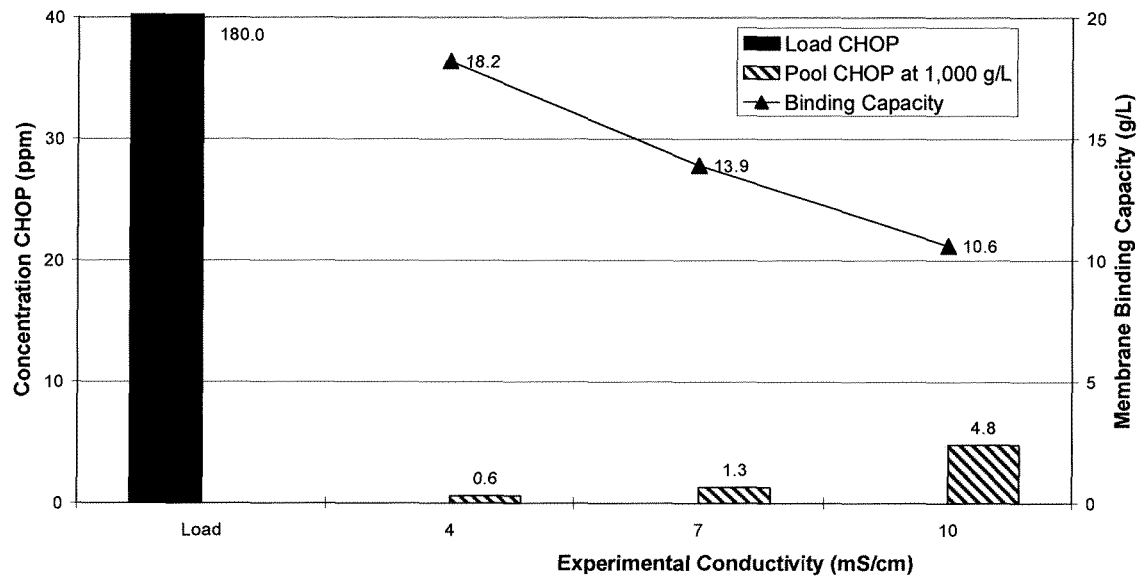
Figure 5: CHOP (bars) and binding capacity (line) for mAb 3 at pH 8.0, Mustang™ Q (Small-scale, 0.35 mL MV, 600 MV/hour).
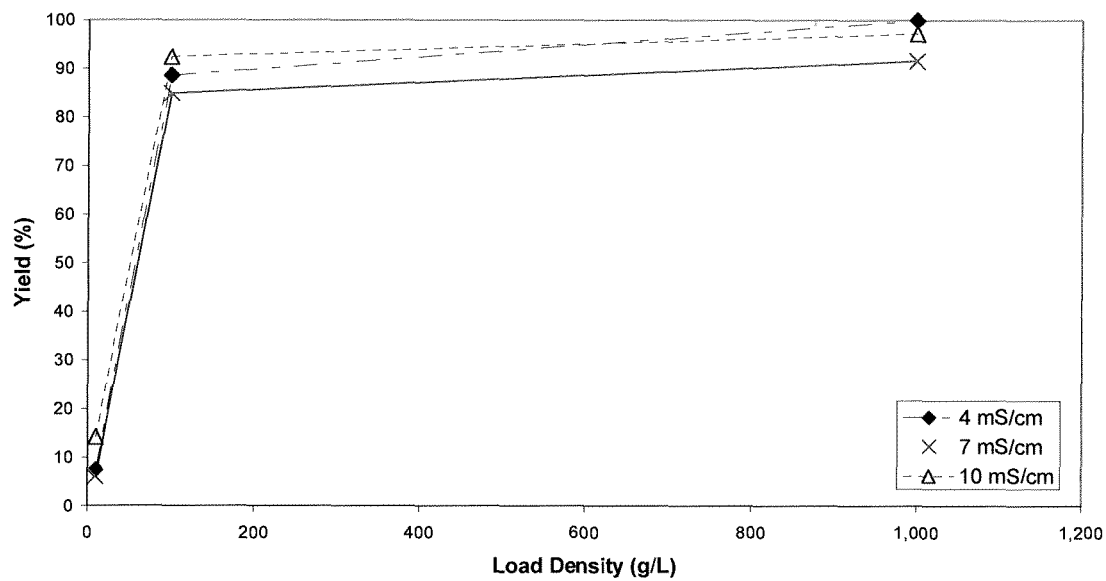
Figure 6: Yield for mAb 3 cation exchange pool at pH 8.0, Mustang™ Q (Small-scale, 0.35 mL MV, 600 MV/hour).

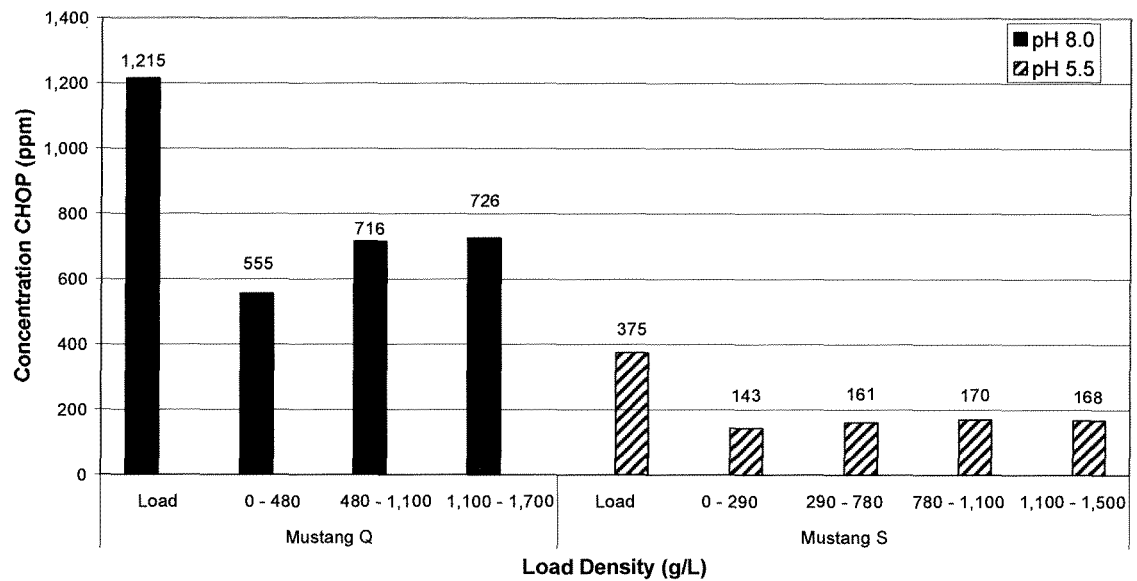

Figure 7: CHOP levels for mAb 4 at pH 8.0 and 4.0 mS/cm, Mustang™ Q (small-scale, 0.18 mL MV, 1333 MV/hour) and then pH 5.5 and 6.1 mS/cm, Mustang™ S (small-scale, 0.18 mL MV, 1333 MV/hour).

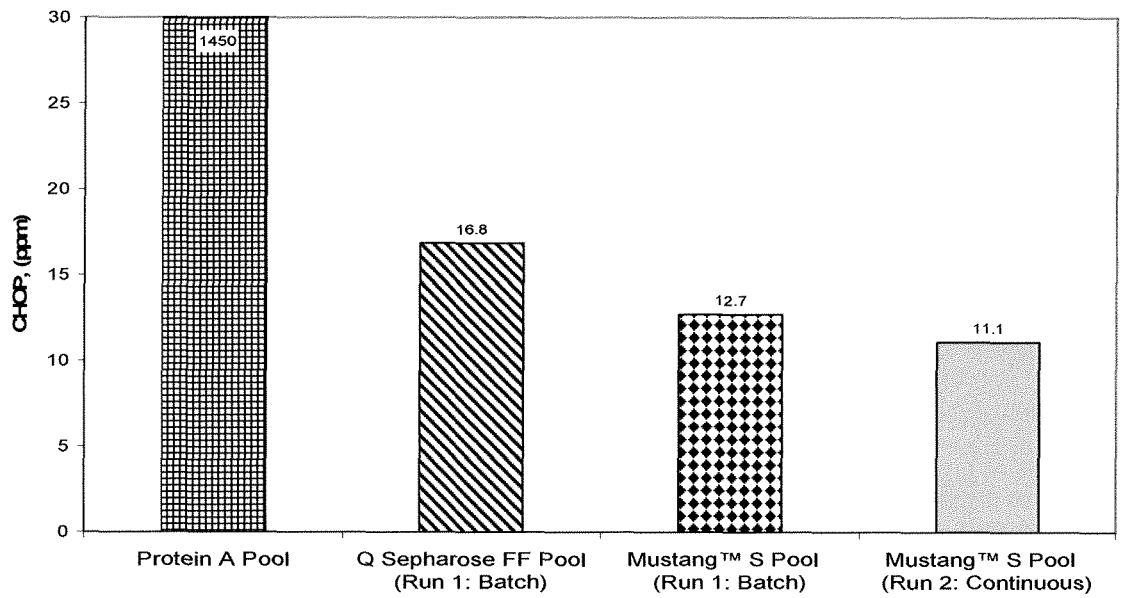

Figure 8: CHOP clearance for mAb 1 at pH 8.0 and 4.7 mS/cm over a Q Sepharose Fast Flow column run in flow-through mode at 100 cm/hour (stripes) and then further purified over Mustang™ S in batch (diamonds) and continuous (solid gray) mode at approximately pH 5.5 and 6 mS/cm (small-scale, 0.18 mL MV, 538 MV/hour).

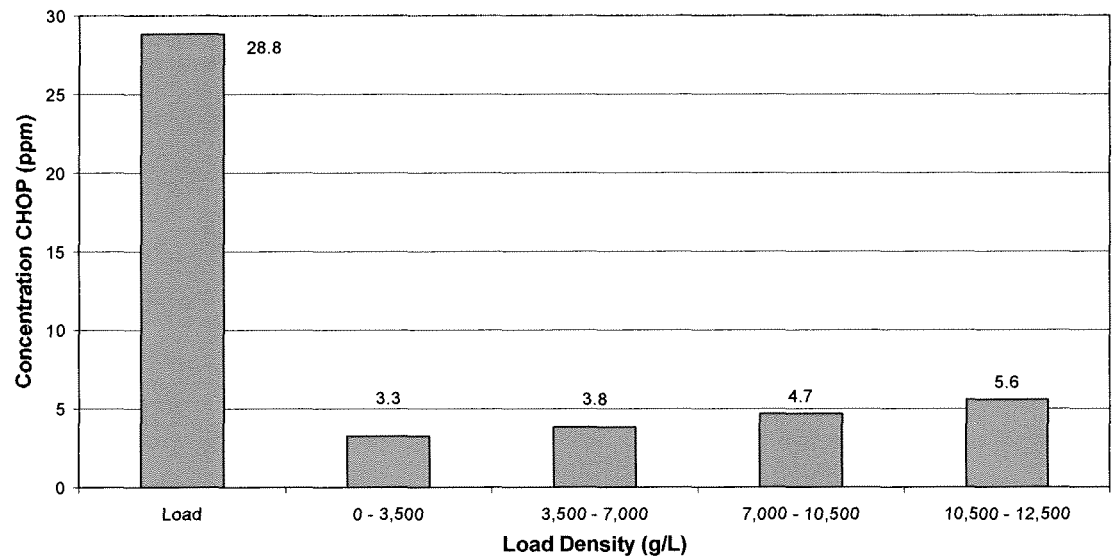
Figure 9: CHOP clearance for mAb 1 at pH 5.5 and 6 mS/cm, Sartobind™ S (small-scale, 0.14 mL MV, 857 MV/hour).
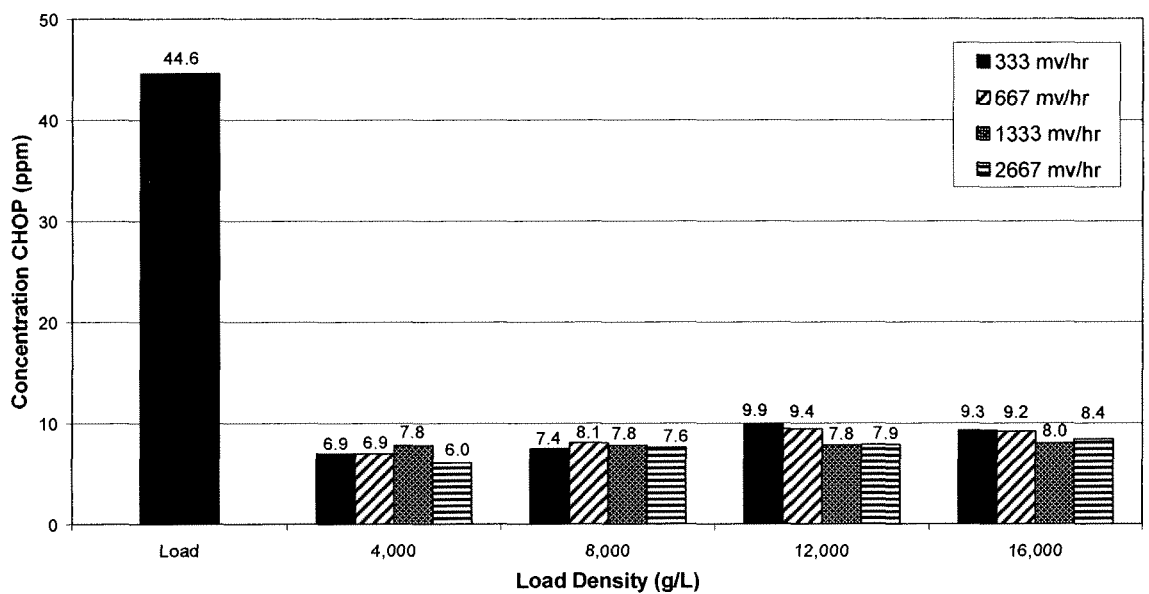
Figure 10: CHOP clearance for mAb 1 at pH 5.5 and 6 mS/cm, Mustang™ S (small-scale, 0.18 mL MV).

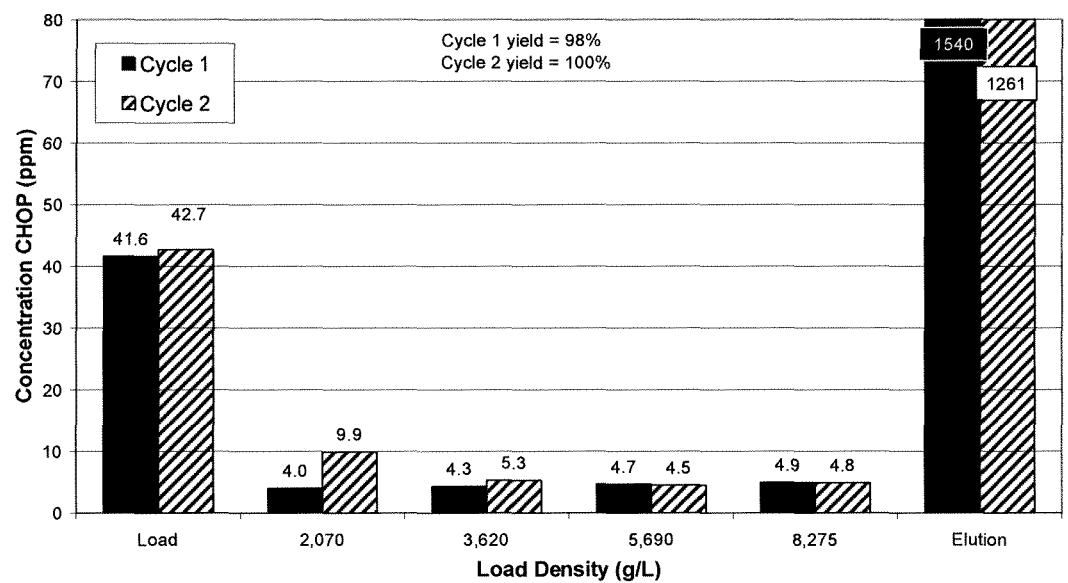
Figure 11: CHOP clearance for mAb 1 at pH 5.5 and 6 mS/cm, Mustang™ S (Pilot-scale, 10 mL MV, 546 MV/hour).

METHODS FOR REMOVING A CONTAMINANT USING INDIGENOUS PROTEIN DISPLACEMENT ION EXCHANGE MEMBRANE CHROMATOGRAPHY

CROSS-REFERENCE TO RELATED APPLICATIONS

This application is a National Stage Application under 35 U.S.C. 371 of International Application No. PCT/US2008/073179 filed Aug. 14, 2008, the contents of which is incorporated herein by reference in its entirety.

FIELD OF THE INVENTION

This invention relates generally to protein purification. In particular, the invention relates to methods for removing a contaminant using indigenous protein displacement ion exchange membrane chromatography.

BACKGROUND OF THE INVENTION

The large-scale, economic purification of proteins is an increasingly important problem for the biotechnology industry. Generally, proteins are produced by cell culture, using either eukaryotic or prokaryotic cell lines engineered to produce the protein of interest by insertion of a recombinant plasmid containing the gene for that protein. Since the cells typically used are living organisms, they must be fed with a complex growth medium, containing sugars, amino acids, and growth factors, usually supplied from preparations of animal serum. Separation of the desired protein from the mixture of compounds fed to the cells and from the by-products of the cells themselves to a purity sufficient for use as a human therapeutic poses a formidable challenge.

Procedures for purification of proteins from cell debris initially depend on the site of expression of the protein. Some proteins can be caused to be secreted directly from the cell into the surrounding growth media; others are made intracellularly. For the latter proteins, the first step of a purification process involves lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. The same problem arises, although on a smaller scale, with directly secreted proteins due to the natural death of cells and release of intracellular host cell proteins in the course of the protein production run.

Once a clarified solution containing the protein of interest has been obtained, its separation from the other proteins produced by the cell is usually attempted using a combination of different chromatography techniques. These techniques separate mixtures of proteins on the basis of their charge, degree of hydrophobicity, or size. Several different chromatography resins are available for each of these techniques, allowing accurate tailoring of the purification scheme to the particular protein involved. The essence of each of these separation methods is that proteins can be caused either to move at different rates down a long column, achieving a physical separation that increases as they pass further down the column, or to adhere selectively to the separation medium, being then differentially eluted by different solvents. In some cases, the desired protein is separated from impurities when the impurities specifically adhere to the column, and the protein of interest does not, that is, the protein of interest is present in the "flow-through".

Publications concerning protein purification include Fahrner et al., Biotechnol Genet Eng Rev. 2001; 18:301-27.

A typical large-scale purification process is often built around the employment of immobilized protein A as the primary capture and purification step in combination with other column Operations. Protein A column operations in general deliver a product-related purity over 98% with most process impurities washed away in the flow-through fraction. Because of this, the ensuing process operational units are considered to be concentrating, purifying, or polishing steps, responsible for separation of product-related isomers and removal of remaining amounts of host cell proteins/DNA, leached protein A, and viruses.

SUMMARY OF THE INVENTION

The invention herein concerns methods for purifying a polypeptide from a composition comprising the polypeptide and at least one contaminant, which methods comprise the sequential steps of: (a) passing the composition through an ion exchange membrane, where the polypeptide and the membrane have opposite charge, at operating conditions comprised of a buffer having a pH sufficiently distinct from the pI of the polypeptide to enhance the charge of the polypeptide and a low ionic strength effective to prevent the shielding of charges by buffer ions, which cause the membrane to bind the polypeptide and the at least one contaminant, and (b) recovering the purified polypeptide from the effluent.

In one alternative, the invention concerns a method for purifying a polypeptide from a composition comprising the polypeptide and at least one contaminant, which method comprises the sequential steps of: (a) passing the composition through a cation exchange membrane, where the polypeptide and the membrane have opposite charge, at operating conditions comprised of a buffer having a pH of about 1 to about 5 pH units below the pI of the polypeptide and a conductivity of ≤about 40 mS/cm, which cause the membrane to bind the polypeptide and the at least one contaminant, and (b) recovering the purified polypeptide from the effluent.

In another alternative, the invention concerns a method for purifying a polypeptide from a composition comprising the polypeptide and at least one contaminant, which method comprises the sequential steps of: (a) passing the composition through an anion exchange membrane, where the polypeptide and the membrane have opposite charge, at operating conditions comprised of a buffer having a pH of about 1 to about 5 pH units above the pI of the polypeptide and a conductivity of ≤about 40 mS/cm, which cause the membrane to bind the polypeptide and the at least one contaminant, and (b) recovering the purified polypeptide from the effluent.

In one aspect, the contaminant is a Chinese Hamster Ovary Protein (CHOP). In another aspect, the polypeptide comprises a CH2/CH3 region. In still another aspect, the polypeptide is an antibody. In yet another aspect, the antibody is a monoclonal antibody.

In other aspects, the methods further comprise subjecting the composition comprising the polypeptide to one or more further purification step(s) either before, during, or after steps a through b, the purification step being, in one alternative, protein A affinity chromatography, and, in another alternative, ion exchange chromatography, using a column or membrane operated in bind/elute, flow-through, or indigenous protein displacement mode.

In addition, the invention provides the preparation of a pharmaceutical composition by combining the purified polypeptide with a pharmaceutically acceptable carrier.

BRIEF DESCRIPTION OF THE DRAWINGS

FIG. 1. CHOP clearance for mAb 1 anion exchange pool at pH 5.5, 6.0 mS/cm, Mustang™ S (Small-scale, 0.18 mL MV, 667 MV/hour).

FIG. 2. CHOP clearance for mAb 2 anion exchange pool at pH 5.5 and 6.4 mS/cm and at pH 8.0 and 5.0 mS/cm, Mustang™ S (Small-scale, 0.18 mL MV, 667 MV/hour).

FIG. 3. Yield for mAb 2 anion exchange pool at pH 5.5 and 6.4 mS/cm and at pH 8.0 and 5.0 mS/cm, Mustang™ S (Small-scale, 0.18 mL MV, 667 MV/hour).

FIG. 4. CHOP clearance for mAb 1 Protein A pool at pH 5.5, 3.2 mS/cm, Mustang™ S (Small-scale, 0.18 mL MV, 1333 MV/hour).

FIG. 5. CHOP (bars) and antibody binding capacity (line) for mAb 3 at pH 8.0, Mustang™ Q (Small-scale, 0.35 mL MV, 600 MV/hour).

FIG. 6. Yield for mAb 3 cation exchange pool at pH 8.0, Mustang™ Q (Small-scale, 0.35 mL MV, 600 MV/hour).

FIG. 7. CHOP levels for mAb 4 at pH 8.0 and 4.0 mS/cm, Mustang™ Q (small-scale, 0.18 mL MV, 1333 MV/hour) and then pH 5.5 and 6.1 mS/cm, Mustang™ S (small-scale, 0.18 mL MV, 1333 MV/hour).

FIG. 8. CHOP clearance for mAb 1 at pH 8.0 and 4.7 mS/cm over a Q Sepharose Fast Flow column run in flow-through mode at 100 cm/hour (stripes) and then further purified over Mustang™ S in batch (diamonds) and continuous (solid gray) mode at approximately pH 5.5 and 6 mS/cm (small-scale, 0.18 mL MV, 538 MV/hour).

FIG. 9. CHOP clearance for mAb 1 at pH 5.5 and 6 mS/cm, Sartobind™ S (small-scale, 0.14 mL MV, 857 MV/hour).

FIG. 10. CHOP clearance for mAb 1 at pH 5.5 and 6 mS/cm, Mustang™ S (small-scale, 0.18 mL MV).

FIG. 11. CHOP clearance for mAb 1 at pH 5.5 and 6 mS/cm, Mustang™ S (Pilot-scale, 10 mL MV, 546 MV/hour).

DETAILED DESCRIPTION OF THE PREFERRED EMBODIMENT

Definitions

Figure 12:
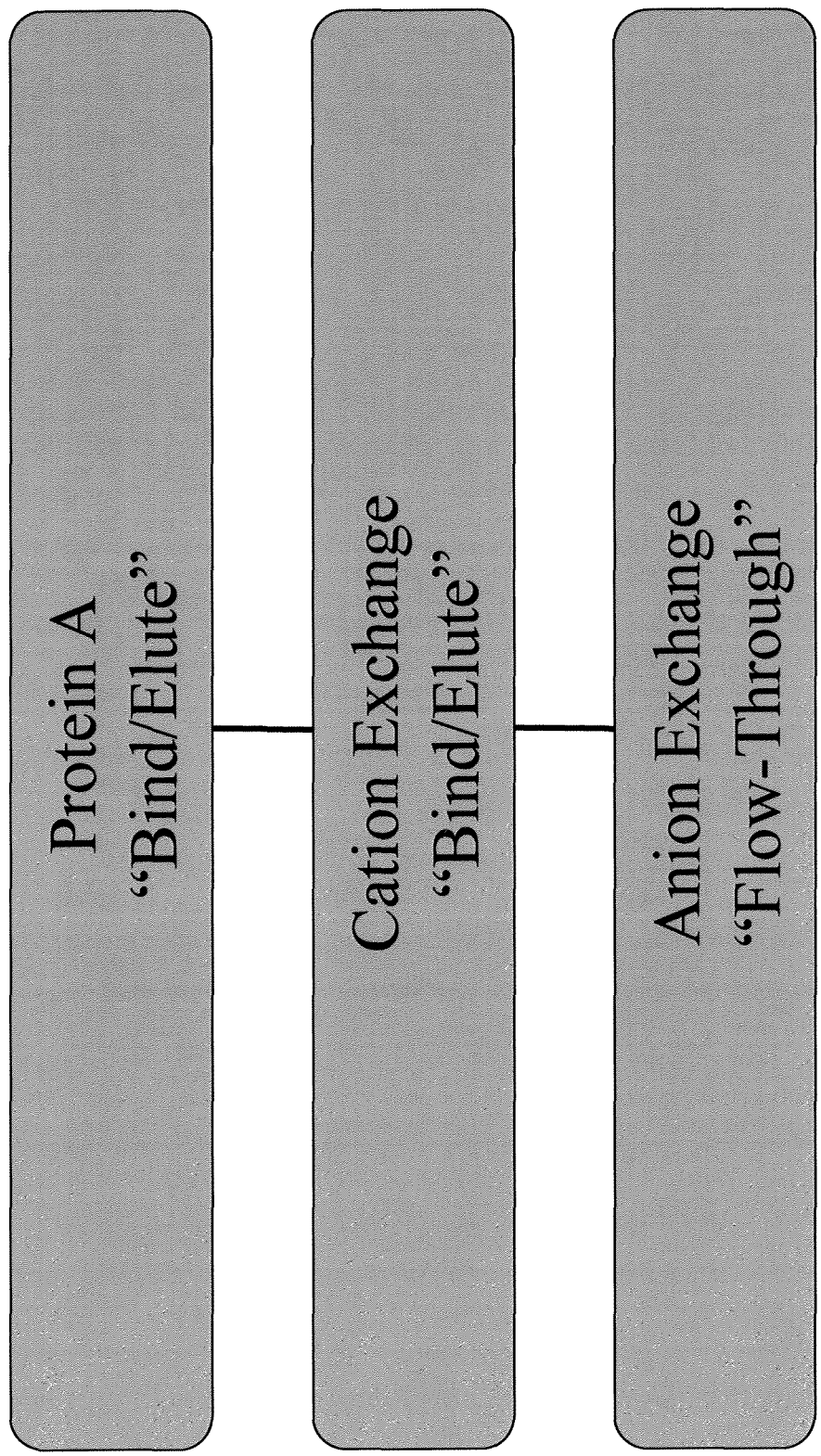
FIG. 12. Outline of protein production in which cation exchange chromatography is run in bind/elute mode.

Herein, numerical ranges or amounts prefaced by the term "about" expressly include the exact range or exact numerical amount.

The "composition" to be purified herein comprises the polypeptide of interest and one or more contaminants. The composition may be "partially purified" (i.e., having been subjected to one or more purification steps, such as protein A chromatography) or may be obtained directly from a host cell or organism producing the antibody (e.g., the composition may comprise harvested cell culture fluid).

As used herein, "polypeptide" refers generally to peptides and proteins having more than about ten amino acids.

Preferably, the polypeptide is a mammalian protein, examples of which include: renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, IGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins (IGFBPs); CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c. CD18, an ICAM, VLA-4 and VCAM; a tumor associated antigen such as HER2, HER3 or HER4 receptor; and fragments and/or variants of any of the above-listed polypeptides as well as antibodies, including antibody fragments, binding to any of the above-listed polypeptides.

A "contaminant" is a material that is different from the desired polypeptide product. The contaminant includes, without limitation: host cell materials, such as Chinese Hamster Ovary Proteins (CHOP); leached protein A; nucleic acid; a variant, fragment, aggregate, isomer or derivative of the desired polypeptide; another polypeptide; endotoxin; viral contaminant; cell culture media component (e.g., garamycin; GENTAMYCIN®) etc.

A polypeptide of interest herein is one which comprises a $C_H2/C_H3$ region and therefore is amenable to purification by protein A affinity chromatography. The term "$C_H2/C_H3$ region" when used herein refers to those amino acid residues in the Fc region of an immunoglobulin molecule which interact with protein A. In preferred embodiments, the $C_H2/C_H3$ region comprises an intact $C_H2$ region followed by an intact $C_H3$ region, and most preferably a Fc region of an immunoglobulin. Examples of $C_H2/C_H3$ region-containing polypeptides include antibodies, immunoadhesins and fusion proteins comprising a polypeptide of interest fused to, or conjugated with, a $C_H2/C_H3$ region.

In preferred embodiments of the invention, the antibody to be purified herein is a recombinant antibody. A "recombinant antibody" is one which has been produced in a host cell which has been transformed or transfected with nucleic acid encoding the antibody, or produces the antibody as a result of homologous recombination. "Transformation" and "transfection" are used interchangeably to refer to the process of introducing nucleic acid into a cell. Following transformation or transfection, the nucleic acid may integrate into the host cell genome, or may exist as an extrachromosomal element. The "host cell" includes a cell in in vitro cell culture as well as a cell within a host animal. Methods for recombinant production of polypeptides are described in U.S. Pat. No. 5,534,615, expressly incorporated herein by reference, for example.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they retain, or are modified to comprise, a $C_H2/C_H3$ region as herein defined.

The antibody herein is directed against an "antigen" of interest. Preferably, the antigen is a biologically important polypeptide and administration of the antibody to a mammal suffering from a disease or disorder can result in a therapeutic benefit in that mammal. However, antibodies directed against non-polypeptide antigens (such as tumor-associated glycolipid antigens; see U.S. Pat. No. 5,091,178) are also contemplated. Where the antigen is a polypeptide, it may be a transmembrane molecule (e.g., receptor) or ligand such as a growth factor. Exemplary antigens include those polypeptides discussed above. Preferred molecular targets for antibodies encompassed by the present invention include CD polypeptides such as CD3, CD4, CD8, CD19, CD20 and CD34; members of the HER receptor family such as the EGF receptor (HER1), HER2, HER3 or HER4 receptor; cell adhesion molecules such as LFA-1 Mac1, p150,95, VLA-4, ICAM-1, VCAM and av/b3 integrin including either a or b subunits thereof (e.g., anti-CD11a, anti-CD18 or anti-CD11b antibodies); growth factors such as VEGF; IgE; blood group antigens; flk2/flt3 receptor; obesity (OB) receptor; mpl receptor; CTLA-4; polypeptide C etc. Soluble antigens or fragments thereof, optionally conjugated to other molecules, can be used as immunogens for generating antibodies. For transmembrane molecules, such as receptors, fragments of these (e.g., the extracellular domain of a receptor) can be used as the immunogen. Alternatively, cells expressing the transmembrane molecule can be used as the immunogen. Such cells can be derived from a natural source (e.g., cancer cell lines) or may be cells which have been transformed by recombinant techniques to express the transmembrane molecule.

Examples of antibodies to be purified herein include, but are not limited to: HER2 antibodies including trastuzumab (HERCEPTIN®) (Carter et al., *Proc. Natl. Acad. Sci. USA*, 89:4285-4289 (1992), U.S. Pat. No. 5,725,856) and pertuzumab (OMNITARG™) (WO01/00245); CD20 antibodies (see below); IL-8 antibodies (St John et al., *Chest*, 103:932 (1993), and International Publication No. WO 95/23865); VEGF or VEGF receptor antibodies including humanized and/or affinity matured VEGF antibodies such as the humanized VEGF antibody huA4.6.1 bevacizumab (AVASTIN®) and ranibizumab (LUCENTIS®) (Kim et al., *Growth Factors*, 7:53-64 (1992), International Publication No. WO 96/30046, and WO 98/45331, published Oct. 15, 1998); PSCA antibodies (WO01/40309); CD11a antibodies including efalizumab (RAPTIVA®) (U.S. Pat. No. 5,622, 700. WO 98/23761, Steppe et al., *Transplant Intl.* 4:3-7 (1991), and Hourmant et al., *Transplantation* 58:377-380 (1994)); antibodies that bind IgE including omalizumab (XOLAIR®) (Presta et al., *J. Immunol.* 151:2623-2632 (1993), and International Publication No. WO 95/19181; U.S. Pat. No. 5,714,338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714,338); CD18 antibodies (U.S. Pat. No. 5,622,700, issued Apr. 22, 1997, or as in WO 97/26912, published Jul. 31, 1997); Apo-2 receptor antibody antibodies (WO 98/51793 published Nov. 19, 1998); Tissue Factor (TF) antibodies (European Patent No. 0 420 937 B1 granted Nov. 9, 1994); $\alpha_4$-$\alpha_7$ integrin antibodies (WO 98/06248 published Feb. 19, 1998); EGFR antibodies (e.g., chimerized or humanized 225 antibody, cetuximab, ERBUTIX® as in WO 96/40210 published Dec. 19, 1996); CD3 antibodies such as OKT3 (U.S. Pat. No. 4,515,893 issued May 7, 1985); CD25 or Tac antibodies such as CH1-621 (SIMULECT®) and ZENAPAX® (See U.S. Pat. No. 5,693,762 issued Dec. 2, 1997); CD4 antibodies such as the cM-7412 antibody (Choy et al., *Arthritis Rheum* 39(1):52-56 (1996)); CD52 antibodies such as CAMPATH-1H (ILEX/Berlex) (Riechmann et al., *Nature* 332: 323-337 (1988)); Fc receptor antibodies such as the M22 antibody directed against Fc(RI as in Graziano et al., *J. Immunol.* 155(10):4996-5002 (1995)); carcinoembryonic antigen (CEA) antibodies such as hMN-14 (Sharkey et al., *Cancer Res.* 55(23Suppl): 5935s-5945s (1995)); antibodies directed against breast epithelial cells including huBrE-3, hu-Mc 3 and CHL6 (Ceriani et al., *Cancer Res.* 55(23): 5852s-5856s (1995); and Richman et al., *Cancer Res.* 55(23 Supp): 5916s-5920s (1995)); antibodies that bind to colon carcinoma cells such as C242 (Litton et al., *Eur J. Immunol.* 26(1):1-9 (1996)); CD38 antibodies, e.g., AT 13/5 (Ellis et al., *J. Immunol.* 155(2):925-937 (1995)); CD33 antibodies such as Hu M195 (Jurcic et al., *Cancer Res* 55(23 Suppl): 5908s-5910s (1995)) and CMA-676 or CDP771; EpCAM antibodies such as 17-1A (PANOREX®); GpIIb/IIIa antibodies such as abciximab or c7E3 Fab (REOPRO®); RSV antibodies such as MEDI-493 (SYNAGIS®); CMV antibodies such as PROTOVIR®; HIV antibodies such as PRO542; hepatitis antibodies such as the Hep B antibody OSTAVIR®; CA 125 antibody OvaRex; idiotypic GD3 epitope antibody BEC2; $\alpha\nu\beta3$ antibody (e.g., VITAXIN®; Medimmune); human renal cell carcinoma antibody such as ch-G250; ING-1; anti-human 17-1An antibody (3622W94); anti-human colorectal tumor antibody (A33); anti-human melanoma antibody R24 directed against GD3 ganglioside; anti-human squamous-cell carcinoma (SF-25); human leukocyte antigen (HLA) antibody such as Smart ID10 and the anti-HLA DR antibody Oncolym (Lym-1); CD37 antibody such as TRU 016 (Trubion); IL-21 antibody (Zymogenetics/Novo Nordisk); anti-B cell antibody (Impheron); B cell targeting MAb (Immunogen/Aventis); 1D09C3 (Morphosys/GPC); LymphoRad 131 (HGS); Lym-1 antibody, such as Lym-1Y-90 (USC) or anti-Lym-1 Oncolym (USC/Peregrine); L1F 226 (Enhanced Lifesci.); BAFF antibody (e.g., WO 03/33658); BAFF receptor antibody (see e.g., WO 02/24909); BR3 antibody; Blys antibody such as belimumab; LYMPHOSTAT-B™; ISF 154 (UCSD/Roche/Tragen); gomiliximab (Idec 152; Biogen Idec); IL-6 receptor antibody such as atlizumab (ACTEMRA™; Chugai/Roche); IL-15 antibody such as HuMax-Il-15 (Genmab/Amgen); chemokine receptor antibody, such as a CCR2 antibody (e.g., MLN1202; Millieneum); anti-complement antibody, such as C5 antibody (e.g., eculizumab, 5G1.1; Alexion); oral formulation of human immunoglobulin (e.g., IgPO; Protein Therapeutics); IL-12 antibody such as ABT-874 (CAT/Abbott); Teneliximab (BMS-224818; BMS); CD40 antibodies, including S2C6 and humanized variants thereof (WO00/75348) and TNX 100 (Chiron/Tanox); TNF-α antibodies including cA2 or infliximab (REMICADE®), CDP571, MAK-195, adalimumab (HUMIRA™), pegylated TNF-α antibody fragment such as CDP-870 (Celltech), D2E7 (Knoll), anti-TNF-α polyclonal antibody (e.g., PassTNF; Verigen); CD22 antibodies such as LL2 or epratuzumab (LYMPHOCIDE®; Immunomedics), including epratuzumab Y-90 and epratzumab I-131, Abiogen's CD22 antibody (Abiogen, Italy), CMC 544 (Wyeth/Celltech), combotox (UT Soutwestern), BL22 (NIH), and LympoScan Tc99 (Immunomedics).

Examples of CD20 antibodies include: "C2B8," which is now called "rituximab" ("RITUXAN®") (U.S. Pat. No. 5,736,137); the yttrium-[90]-labelled 2B8 murine antibody designated "Y2B8" or "Ibritumomab Tiuxetan" (ZEVALIN®) commercially available from IDEC Pharmaceuticals, Inc. (U.S. Pat. No. 5,736,137; 2B8 deposited with ATCC under accession no. HB11388 on Jun. 22, 1993); murine IgG2a "B1," also called "Tositumomab," optionally labelled with $^{131}$I to generate the "131I-B1" or "iodine I131 tositumomab" antibody (BEXXAR™) commercially available from Corixa (see, also, U.S. Pat. No. 5,595,721); murine monoclonal antibody "1F5" (Press et al., Blood 69(2):584-591. (1987)) and variants thereof including "framework patched" or humanized 1F5 (WO 2003/002607, Leung, S.; ATCC deposit HB-96450); murine 2H7 and chimeric 2H7 antibody (U.S. Pat. No. 5,677,180); humanized 2147 (WO 2004/056312, Lowman et al.,); 2F2 (HuMax-CD20), a fully human, high-affinity antibody targeted at the CD20 molecule in the cell membrane of B-cells (Genmab, Denmark; see, for example, Glennie and van de Winkel, *Drug Discovery Today* 8: 503-510 (2003) and Cragg et al., *Blood* 101: 1045-1052 (2003); WO 2004/035607; US2004/0167319); the human monoclonal antibodies set forth in WO 2004/035607 and US2004/0167319 (Teeling et al.,); the antibodies having complex N-glycoside-linked sugar chains bound to the Fe region described in US 2004/0093621 (Shitara et al.,); monoclonal antibodies and antigen-binding fragments binding to CD20 (WO 2005/000901, Tedder et al.,) such as HB20-3, HB20-4, HB20-25, and MB20-11; CD20 binding molecules such as the AME series of antibodies, e.g., AME 33 antibodies as set forth in WO 2004/103404 and US2005/0025764 (Watkins et al., Eli Lilly/Applied Molecular Evolution, AME); CD20 binding molecules such as those described in US 2005/0025764 (Watkins et al.,); A20 antibody or variants thereof such as chimeric or humanized A20 antibody (cA20, hA20, respectively) or IMMU-106 (US 2003/0219433, Immunomedics); CD20-binding antibodies, including epitope-depleted Leu-16, 1H4, or 2B8, optionally conjugated with IL-2, as in US 2005/0069545A1 and WO 2005/16969 (Carr et al.,); bispecific antibody that binds CD22 and CD20, for example, hLL2xhA20 (WO2005/14618, Chang et al.,); monoclonal antibodies L27, G28-2, 93-1B3, B-C1 or NU-B2 available from the International Leukocyte Typing Workshop (Valentine et al., In: *Leukocyte Typing* III (McMichael, Ed., p. 440, Oxford University Press (1987)); 1H4 (Haisma et al., *Blood* 92:184 (1998)); anti-CD20 auristatin E conjugate (Seattle Genetics); anti-CD20-IL2 (EMD/Biovation/City of Hope); anti-CD20 MAb therapy (EpiCyte); anti-CD20 antibody TRU 015 (Trubion).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). In a further embodiment, "monoclonal antibodies" can be isolated from antibody phage libraries generated using the techniques described in McCafferty et al., *Nature,* 348:552-554 (1990). Clackson et al., *Nature,* 352:624-628 (1991) and Marks et al., *J. Mol. Biol.,* 222:581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nuc. Acids. Res.,* 21:2265-2266 (1993)). Thus, these techniques are viable alternatives to traditional monoclonal antibody hybridoma techniques for isolation of monoclonal antibodies. Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggermann et al., *Year in Immuno.,* 7:33 (1993); and Duchosal et al., *Nature* 355:258 (1992).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

The term "hypervariable region" when used herein refers to the amino acid residues of an antibody which are responsible for antigen-binding. The hypervariable region comprises amino acid residues from a "complementarity determining region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Polypeptides of Immunological Interest*, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework" or "FR" residues are those variable domain residues other than the hypervariable region residues as herein defined.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 (1993); Chothia et al., *J. Mol. Biol.*, 196:901 (1987)).

Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immnol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments. Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science*, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163-167 (1992)). In another embodiment, the F(ab')$_2$ is formed using the leucine zipper GCN4 to promote assembly of the F(ab')$_2$ molecule. According to another approach, F(ab')$_2$ fragments can be isolated directly from recombinant host cell culture. Other techniques for the production of antibody fragments will be apparent to the skilled practitioner.

In other embodiments, the antibody of choice is a single chain Fv fragment (scFv). See WO 93/16185. "Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies*, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444-6448 (1993).

The expression "linear antibodies" when used throughout this application refers to the antibodies described in Zapata et al., *Polypeptide Eng.* 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

"Multispecific antibodies" have binding specificities for at least two different epitopes, where the epitopes are usually from different antigens. While such molecules normally will only bind two antigens (i.e., bispecific antibodies, BsAbs), antibodies with additional specificities such as trispecific antibodies are encompassed by this expression when used herein. Examples of BsAbs include those with one arm directed against a tumor cell antigen and the other arm directed against a cytotoxic trigger molecule such as anti-FcγRI/anti-CD15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell ahesion molecule (NCAM)/anti-CD3, anti-folate binding protein (FBP)/anti-CD3, anti-pan carcinoma associated antigen (AMOC-31)/anti-CD3; BsAbs with one arm which binds specifically to a tumor antigen and one arm which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α(IFN-α)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); BsAbs which can be used as fibrinolytic agents such as anti-fibrin/anti-tissue plasminogen activator (tPA), anti-fibrin/anti-urokinase-type plasminogen activator (uPA); BsAbs for targeting immune complexes to cell surface receptors such as anti-low density lipoprotein (LDL)/anti-Fc receptor (e.g., FcγRI, or FcγRIII); BsAbs for use in therapy of infectious diseases such as anti-CD3/anti-herpes simplex virus (INV), anti-T-cell receptor:CD3 complex/anti-influenza, anti-FcγR/anti-IIIV; BsAbs for tumor detection in vitro or in vivo such as anti-CEA/anti-EOTUBE, anti-CEA/anti-DPTA, anti-p185$^{HER2}$/anti-hapten; BsAbs as vaccine adjuvants; and BsAbs as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase. Examples of trispecific antibodies include anti-CD3/anti-CD4/anti-CD37, anti-CD3/anti-CD5/anti-CD37 and anti-CD3/anti-CD8/anti-CD37. Bispecific antibodies can be prepared as full length antibodies or antibody fragments (e.g., F(ab')$_2$ bispecific antibodies).

Antibodies with more than two valencies are contemplated. For example, trispecific antibodies can be prepared. Tutt et al., *J. Immunol.* 147: 60 (1991).

A "naked antibody" for the purposes herein is an antibody that is not conjugated to a cytotoxic moiety or radiolabel.

An "intact antibody" herein is one which comprises two antigen binding regions, and an Fc region. Preferably, the intact antibody has a functional Fc region.

"Treatment" refers to both therapeutic treatment and prophylactic or preventative measures. Those in need of treatment include those already with the disorder as well as those in which the disorder is to be prevented.

A "disorder" is any condition that would benefit from treatment with the antibody purified as described herein. This includes both chronic and acute disorders and diseases and those pathological conditions which predispose the mammal to the disorder in question.

The phrase "ion exchange chromatography" refers to a separation technique in which compounds are separated based on their net charge. Molecules are classified as either anions (having a negative charge) or cations (having a positive charge). Some molecules (e.g., polypeptides) may have both anionic and cationic groups.

An ion exchange chromatography membrane will bind a compound with an overall positive or negative charge. Binding sites are located along the pores of the adsorber. The compound is transported to the binding site by convection. A positively charged membrane (anion exchanger) will bind a compound with an overall negative charge. Conversely, a negatively charged membrane (cation exchanger) will bind a compound with an overall positive charge.

Ion exchange membranes can be further categorized as either strong or weak. Strong ion exchange membranes are charged (ionized) across a wide range of pH levels. Weak ion exchange membranes are ionized within a narrow pH range. The four most common ion exchange chemistries are:

| Type of Ion Exchange | Common Abbreviation | Functional Group |
| --- | --- | --- |
| Strong Anion | Q | Quarternary Ammonium |
| Weak Anion | D | Diethylamine |
| Strong Cation | S | Sulfonic Acid |
| Weak Cation | C | Carboxylic Acid |

In general, ion exchange membranes have pore sizes of 0.1 to 100 µm. As a reference, Sartobind Q (Sartorius AG) is a strong anion exchange membrane having a nominal pore size of 3-5 µm and is commercially available in a single or multiple layer format, and Mustang Q (Pall Corporation) is a strong anion exchange membrane having a nominal pore size of 0.8 µm and is likewise commercially available in a single or multiple layer format. As another reference, Sartobind S (Sartorius AG) is a strong cation exchange membrane having a nominal pore size of 3-5 µm and is commercially available in a single or multiple layer format, and Mustang S (Pall Corporation) is a strong cation exchange membrane having a nominal pore size of 0.8 µm and is similarly commercially available in a single or multiple layer format.

A "nominal" pore size rating describes the ability of the membrane to retain the majority of particulates at 60 to 98% the rated pore size.

The "pH" of a solution measures the acidity or alkalinity relative to the ionization of a water sample. The pH of water is neutral, i.e., 7. Most pH readings range from 0 to 14. Solutions with a higher [H+] than water (pH less than 7) are acidic; solutions with a lower [H+] than water (pH greater than 7) are basic or alkaline. pH can be measured using a pH meter. Buffer pH may be adjusted using an acid or base like HCl or NaOH.

The "pI" or "isoelectric point" of a molecule such as a polypeptide refers to the pH at which the polypeptide contains an equal number of positive and negative charges. The pI can be calculated from the net charge of the amino acid residues of the polpeptide or can be determined by isoelectric focusing. The amphoteric nature of polypeptides to have both anionic and cationic groups may be manipulated. The pH of a polypeptide may be lowered to the point where the desired polypeptide behaves as a cation (having a positive charge). Alternatively, the pH of a polypeptide may be increased to the point where the desired polypeptide behaves as an anion (having a negative charge).

The term "conductivity" refers to the ability of a solution to conduct an electric current between two electrodes. The basic unit of conductivity is the siemens (S), formerly called the mho. Conductivity is commonly expressed in units of mS/cm. Since the charge on ions in solution facilities the conductance of electrical current, the conductivity of a solution is proportional to its ion concentration. Both these measurements correlate well with the ionic strength. Ionic strength is closely related to the concentration of electrolytes and indicates how effectively the charge on a particular ion is shielded or stabilized by other ions in an electrolyte. The main difference between ionic strength and electrolyte concentration is that the former is higher if some of the ions are more highly charged. Another difference between the two is that ionic strength reflects the concentration of free ions, and not just of how much salt was added to a solution. Conductivity can be measured using a conductivity meter, such as various models of Orion conductivity meters. Conductivity of a solution may be altered by changing the concentration of ions therein. For example, the concentration of a buffering agent and/or the concentration of a salt (e.g., sodium chloride, sodium acetate, or potassium chloride) in the solution may be altered in order to achieve the desired conductivity. Preferably, the salt concentration of the various buffers is modified to achieve the desired conductivity.

For membrane chromatography, the "flow rate" is usually described as membrane volumes per hour (MV/h).

For membrane chromatography, the "load density" is often expressed as grams of composition processed per liter of membrane.

A "buffer" is a solution that resists changes in pH by the action of its acid-base conjugate components. Various buffers which can be employed depending, for example, on the desired pH of the buffer are described in *Buffers. A Guide for the Preparation and Use of Buffers in Biological Systems*, Gueffroy, D., Ed. Calbiochem Corporation (1975).

By "purifying" an antibody from a composition comprising the antibody and one or more contaminants is meant increasing the degree of purity of the antibody in the composition by removing (completely or partially) at least one contaminant from the composition. A "purification step" may be part of an overall purification process resulting in a "homogeneous" composition. "Homogeneous" is used herein to refer to a composition comprising at least about 70% by weight of the antibody of interest, based on total weight of the composition, preferably at least about 80% by weight, more preferably at least about 90% by weight, even more preferably at least about 95% by weight.

By "binding" a molecule to an ion exchange membrane is meant exposing the molecule to the ion exchange membrane under appropriate conditions (pH and/or conductivity) such that the molecule is reversibly immobilized in or on the ion exchange membrane by virtue of electrostatic interactions between the molecule and a charged group or charged groups of the ion exchange membrane.

By "washing" the ion exchange membrane is meant passing an appropriate buffer through or over the ion exchange membrane.

By "eluting" a molecule (e.g., antibody or contaminant) from an ion exchange membrane is meant to remove the molecule therefrom.

For membrane chromatography, "flow-through" refers to binding of impurities to the membrane while the compound is unretained.

The phrase "mixed mode" refers to a sorbent that has the ability to separate compounds based on two different mechanisms, e.g. a separation based on hydrophilicity/hydrophobicity differences between polypeptides overlaid on a separation based on net charge. This is often accomplished by using a multi-modal ligand that may interact with a target molecule in several different ways including ionic interaction and hydrogen bonding or hydrophobic interaction. Sorbents like GE Healthcare Capto™ MMC and Capto™ Adhere are examples of "mixed mode" chromatography resins.

MODES FOR CARRYING OUT THE INVENTION

The invention herein provides methods for purifying a polypeptide from a composition (e.g., an aqueous solution) comprising the polypeptide and one or more contaminants. The composition is generally one resulting from the recombinant production of the polypeptide, but may be that resulting from production of the polypeptide by peptide synthesis (or other synthetic means) or the polypeptide may be purified from a native source of the polypeptide. Preferably the polypeptide is a $C_H2/C_H3$ region-containing polypeptide. In preferred embodiments, the $C_H2/C_H3$ region-containing polypeptide is an antibody.

Recombinant Production of Antibodies

For recombinant production of the antibody, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence (e.g., as described in U.S. Pat. No. 5,534,615, specifically incorporated herein by reference).

Suitable host cells for cloning or expressing the DNA in the vectors herein are prokaryote, yeast, or higher eukaryotic cells. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of Spodoptera frugiperda cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines include, but are not limited to, monkey kidney CV1 cells transformed by SV40 (COS-7, ATCC CRL 1651); human embryonic kidney cells (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and human hepatoma cells (Hep G2). Often, CHO cells are preferred for the expression of antibodies, and may be advantageously used to produce the antibodies purified in accordance with the present invention.

Host cells are transformed with the above-described expression or cloning vectors for antibody production and cultured in conventional nutrient media modified as appropriate for inducing promoters, selecting transformants, or amplifying the genes encoding the desired sequences.

The host cells used to produce the antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as garamycin; GENTAMYCIN®), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed cells (e.g., resulting from homogenization), is removed, for example, by centrifugation or ultrafiltration. Where the antibody is secreted into the medium, supernatants from such expression systems may be concentrated using a commercially available protein concentration filter, for example, an Amicon or Millipore Pellicon ultrafiltration unit.

The Membrane Ion Exchange Chromatography Method of the Invention

In the preferred embodiment of the invention, the composition to be subjected to the purification method herein is a recombinantly produced antibody, preferably an intact antibody, expressed by a Chinese Hamster Ovary (CHO) recombinant host cell culture. Optionally, the composition has been subjected to at least one purification step prior to membrane ion exchange chromatography. The composition contains the antibody of interest and one or more contaminants, such as Chinese Hamster Ovary Proteins (CHOP); leached protein A; nucleic acid; a variant, fragment, aggregate or derivative of the desired antibody; another polypeptide; endotoxin; viral contaminant; cell culture media component (e.g., garamycin; GENTAMYCIN®), etc.

Examples of additional purification procedures which may be performed prior to, during, or following the membrane ion exchange chromatography method include fractionation on a hydrophobic interaction chromatography (e.g., on PHENYL-SEPHAROSE™), ethanol precipitation, thermal precipitation, polyethylene glycol (PEG) precipitation, isoelectric focusing, Reverse Phase HPLC, chromatography on silica, chromatography on HEPARIN SEPHAROSE™, anion exchange chromatography, cation exchange chromatography, mixed mode ion exchange, chromatofocusing, SDS-PAGE, ammonium sulfate precipitation, hydroxyapatite chromatography, gel electrophoresis, dialysis, hydrophic charge induction chromatography, high performance tangential flow filtration (HPTFF), and affinity chromatography (e.g., using protein A, protein G, an antibody, or a specific substrate, ligand or antigen as the capture reagent).

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or filtration. Where the antibody is secreted into the medium, the recombinant host cells may be separated from the cell culture medium by centrifugation or filtration, for example.

The majority of the purification occurs during protein A affinity chromatography. Protein A is a bacterial cell wall protein that binds specifically to the Fc region of antibodies. When immobilized onto chromatography media, protein A provides a technique for purifying recombinant antibodies because it can selectively bind antibodies in complex solutions, allowing impurities to flow through.

The basic protocol of protein A affinity column is straightforward: bind at about neutral pH and elute at acid pH. Protein A immobilized on a solid phase is used to purify the $C_H2/C_H3$ region-containing polypeptide. The solid phase is preferably a column comprising a glass, silica, or agarose surface for immobilizing the protein A. Preferably, the solid phase is a controlled pore glass column, silicic acid column, or highly cross-linked agarose column. A Mabselect SuRe™ column, commercially available from GE Healthcare, is an example of a highly cross-linked agarose protein A column effective at purifying antibodies. Sometimes, the column has been coated with a reagent, such as glycerol, in an attempt to prevent nonspecific adherence to the column. The PROSEP A™ column, commercially available from Millipore Corporation, is an example of a protein A controlled pore glass column which is coated with glycerol. The solid phase for the protein A chromatography is equilibrated with a suitable buffer.

The contaminated preparation derived from the recombinant host cells is loaded on the equilibrated solid phase using a loading buffer which may be the same as the equilibration buffer. As the contaminated preparation flows through the solid phase, the polypeptide is adsorbed to the immobilized protein A, and other contaminants (such as Chinese Hamster Ovary Proteins, CHOP, where the polypeptide is produced in a CHO cell) bind nonspecifically to the solid phase.

The next step performed sequentially entails removing the contaminants bound to the solid phase by washing the solid phase with a solution containing a salt, amino acid, and/or hydrophobic electrolyte solvent in an intermediate wash step. In preferred embodiments, the salt in this wash is potassium phosphate, the amino acid is arginine, and the hydrophobic electrolyte is TEMAC and/or TEAC. While a single solute may be present in the wash, in certain embodiments, two or more such solutes may be used. The solute(s) are preferably added to a pH buffered solution having a pH at about neutrality.

Following the intermediate wash step of the preceding paragraph, the polypeptide of interest is recovered from the column. This is normally achieved using a suitable elution buffer. The polypeptide may, for example, be eluted from the column using an elution buffer having a low pH, e.g., in the range from about 2 to about 5, and preferably in the range from about 2.5 to about 3.5. Examples of elution buffers for this purpose include citrate or acetate buffers.

Membrane ion exchange chromatography is performed as claimed herein. A decision is first made as to whether an anion or cation exchange membrane is to be employed. Although the isoelectric point (pI) of some antibodies ranges from approximately 6.7 to 9.4, the pI of many antibodies is high (often >8 and sometimes >9). In general, a cation exchange membrane may be used for antibodies with pI's greater than about 8, and an anion exchange membrane may be used for antibodies with pI's less than about 8.

For membrane cation exchange chromatography run in indigenous protein displacement mode, the pH of the load material is adjusted to about 1 to about 5 pH units below the pI of the antibody, the conductivity of the load material is adjusted to ≤about 40 mS/cm, depending on the pH, and the antibody is then pumped through the membrane. In some embodiments, the pH of the load material is adjusted to about 1 to about 4 pH units, about 1 to about 3 pH units, about 1 to about 2 pH units, or about 1 pH unit, below the pI of the antibody. In other embodiments, the conductivity of the load material is adjusted to ≤about 20 mS/cm or ≤about 10 mS/cm, depending on the pH. Because the pH of the load is less than the pI of the antibody, the antibody (which has become positively charged) will NOT flow through initially. Rather, the antibody will be electrostatically bound to the negative functional groups of the cation exchanger. This is because the antibody (positive) and membrane (negative) have opposite charge. Since the pI of many contaminants, e.g., host cell proteins, such as CHOP, that elute with the antibody during protein A affinity chromatography is only slightly different from the pI of the antibody, that is, the pIs may differ by only about 0.05 to about 0.2 pI units, these contaminants, like the "basic" antibodies, will also bind to the membrane. Without being bound by theory, it appears that for membrane cation exchange chromatography run in indigenous protein displacement mode, at pH and conductivity conditions that induce charge with minimal ionic shielding, the contaminants preferentially bind to the membrane, or otherwise effectively "displace" the antibody from the membrane (R R Drager, F E Regnier, J Chromatogr. 359:147-55 (1986)), allowing the antibody to "elute" from the matrix or flow through after binding and be recovered in the effluent.

For membrane anion exchange chromatography run in indigenous protein displacement mode, the pH of the load material is adjusted to about 1 to about 5 pH units above the pI of the antibody, the conductivity of the load material is adjusted to ≤about 40 mS/cm, depending on the pH, and the antibody is then pumped through the membrane. In some embodiments, the pH of the load material is adjusted to about 1 to about 4 pH units, about 1 to about 3 pH units, about 1 to about 2 pH units, or about 1 pH unit, above the pI of the antibody. In other embodiments, the conductivity of the load material is adjusted to ≤about 20 mS/cm or ≤about 10 mS/cm, depending on the pH. Because the pH of the load is greater than the pI of the antibody, the antibody (which has become negatively charged) will NOT flow through initially. Rather, the antibody will be electrostatically bound to the positive functional groups of the anion exchanger. This is because the antibody (negative) and membrane (positive) have opposite charge. Since the pI of many contaminants, e.g., host cell proteins, such as CHOP, that elute with the antibody during protein A affinity chromatography is only slightly different from the pI of the antibody, that is, the pIs may differ by only about 0.05 to about 0.2 pI units, these contaminants, like the "acidic" antibodies, will also bind to the membrane. Without being bound by theory, it appears that for membrane anion exchange chromatography run in indigenous protein displacement mode, at pH and conductivity conditions that induce charge with minimal ionic shielding, the contaminants preferentially bind to the membrane, or otherwise effectively "displace" the antibody from the membrane (R R Drager, F E Regnier, J Chromatogr. 359:147-55 (1986)), allowing the antibody to "elute" from the matrix or flow through after binding and be recovered in the effluent.

In one example, membrane chromatography is run on either a standard chromatography system or a custom chromatography system like an AKTA™ Explorer (GE Healthcare) equipped with pressure gauges, sensors, and pump plus pump controllers. In this example, the membrane device is installed downstream of a pressure gauge. In said example, the pH and conductivity detectors are installed downstream of the membrane device. Continuing with this example, the system is thoroughly flushed with water and then with equilibration buffer before the installation of the membrane. Continuing further with the example, the system with the membrane is flushed with equilibration buffer until the solution pH and conductivity outlet match the equilibration buffer specification (about five membrane volumes) and a stable baseline is observed. Continuing even further with this example, the feed material is loaded by a pump at 333-2667 MV/hour, pH 5.5 (for purification of a hypothetical "basic" antibody) or pH 8.0 (for purification of a hypothetical "acidic" antibody), and a conductivity of approximately 4 mS/cm. Continuing still further with this example, the operation backpressure, and pH and conductivity changes during the operation are recorded. Finally, in this example, the polypeptide in the membrane effluent is collected immediately when an ultraviolet (UV) absorbance trace at 280 nm is 0.2 absorbance units over the baseline, the pool collection is stopped once the UV trace at 280 nm is below 0.2 absorbance units, and the samples from the pool in the membrane effluent fraction are assayed for polypeptide concentration, dimer/aggregation level, host cell proteins, DNA, and leached protein A. The step recovery is typically calculated using the polypeptide loaded and the polypeptide in the membrane effluent. The membrane is traditionally one-time-use only.

Regarding analytical assays, polypeptide content (antibody concentration) may be determined by absorbance at 280 nm using a Beckman spectrophotometer. Antibody aggregation may be determined by size-exclusion chromatography. Host cell protein, e.g., CHOP, levels may be analyzed by an enzyme-linked immunosorbent assay (ELISA). Host-cell DNA may be quantitated by employment of TaqMAN PCR (polymerase chain reaction). Leached protein A may be performed using the immunochemical ELISA-based method recommended by the protein A resin vendor.

The following buffers are hypothetically designed and tested for use with the S membrane: (1) 89 mM acetic acid, 127 mM TRIS base, 21 mM citric acid, pH 5.5, 6.0 mS/cm, (2) 28 mM MES, 95 mM NaCl, pH 6.0, 11 mS/cm, (3) 200 mM NaOAc, pH 5.5, 12 mS/cm, (4) 100 mM NaOAc, pH 5.5, 6.4 mS/cm, and (5) 96 mM acetic acid, 65 mM TRIS, pH 5.0, 3.6 mS/cm.

The following buffers are hypothetically designed and tested for use with the Q membrane: (1) 50 mM TRIS, 15 mM NaCl, pH 8.0, 4.3 mS/cm, (2) 25 mM TRIS, pH 8.0, 1.3 mS/cm, (3) 60 mM TRIS, 118 mM NaCl, pH 8.0, 15.7 mS/cm, (4) 50 mM TRIS, 50 mM NaOAc, pH 8.0, 7.0 mS/cm, (5) 25 mM HEPES, 85 mM NaOAc, pH 7.0, 6.5 mS/cm, and (6) 91 mM acetic acid, 130 mM TRIS, pH 8.0, 5.0 mS/cm.

Additionally, any buffer system can be pH adjusted up or down with the addition of acetic acid, citric acid, HEPES, hydrochloric acid, phosphoric acid, sodium hydroxide, TRIS, or other such acidic and basic buffers to reach a suitable pH. Any buffer system can also be conductivity adjusted up or down using purified water, water for injection (WFI), sodium acetate, sodium chloride, potassium phosphate, or other such low and high salt containing buffers to reach a suitable conductivity.

Development of the indigenous protein displacement membrane chromatography step is straightforward. The load material is run through the membrane at various levels of pH and conductivity. The retention of the polypeptide, either antibody or contaminant, can be enhanced when the molecule has a large electrostatic interaction. Electrostatic interactions can be enhanced when operating under conditions where the polypeptides are highly charged, i.e., when using a buffer having a pH sufficiently distinct from the pI of the polypeptide, enhancing the charge of the polypeptide, and a low ionic strength to prevent the shielding of charges by buffer ions. In contrast, electrostatic interactions can be reduced when operating under conditions where the polypeptides are poorly charged, i.e., when using a buffer having a pH sufficiently close to the pI of the polypeptide, reducing the charge of the polypeptide, and a high ionic strength to permit the shielding of charges by buffer ions. As a result, polypeptides having different physico-chemical properties can be separated by membrane adsorption by optimizing buffer solution. Some molecules can be retained on a given membrane while other ones flow through based on the appropriate selection of the pH and ionic strength of the buffer.

The antibody preparation obtained according to the membrane ion exchange chromatography method herein may be subjected to additional purification steps, if necessary. Exemplary further purification steps have been discussed above.

Referring to FIG. 12, one example of a successful purification scheme is a recovery process entailing an initial fractionation step of protein A affinity chromatography, an intermediate purification step of cation exchange chromatography run in bind/elute mode, and a final polishing step of anion exchange chromatography run in a flow-through mode.

Figure 13:
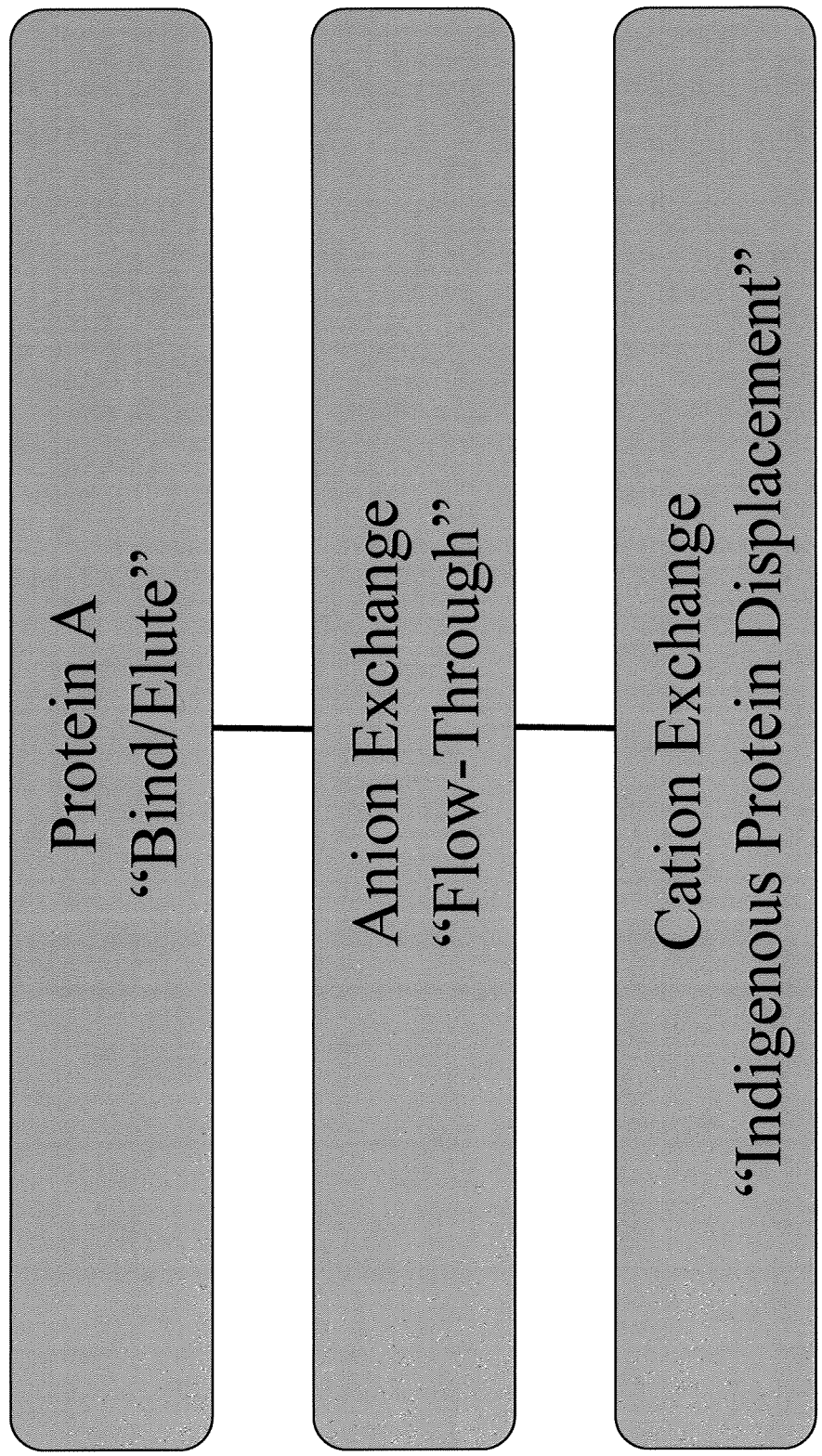
FIG. 13. Outline of protein production replacing the cation exchange chromatography run in bind/elute mode with a cation exchange membrane run in indigenous protein displacement mode.

Referring to FIG. 13, one example of an improved purification scheme is a recovery process entailing the initial fractionation step of protein A affinity chromatography but replacing the cation exchange column chromatography run in bind/elute mode with a cation exchange membrane run in indigenous protein displacement mode. This would be advantageous for many reasons, one reason being that the intermediate and polishing steps could be combined into one continuous operation, that is, a single step.

Optionally, the antibody is conjugated to one or more heterologous molecules as desired. The heterologous molecule may, for example, be one which increases the serum half-life of the antibody (e.g., polyethylene glycol, PEG), or it may be a label (e.g., an enzyme, fluorescent label and/or radionuclide), or a cytotoxic molecule (e.g., a toxin, chemotherapeutic drug, or radioactive isotope etc).

A therapeutic formulation comprising the antibody, optionally conjugated with a heterologous molecule, may be prepared by mixing the antibody having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. "Pharmaceutically acceptable" carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulation to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid.

The antibody purified as disclosed herein or the composition comprising the antibody and a pharmaceutically acceptable carrier is then used for various diagnostic, therapeutic or other uses known for such antibodies and compositions. For example, the antibody may be used to treat a disorder in a mammal by administering a therapeutically effective amount of the antibody to the mammal.

The following example(s) are offered by way of illustration and not by way of limitation. The disclosures of all citations in the specification are expressly incorporated herein by reference.

EXAMPLES

Introduction

Bioreactor titers for monoclonal antibodies (mAbs) are increasing as cell culture conditions improve. Larger batches of mAbs may be difficult to purify using traditional column chromatography. New resins with increased binding capacities may not be sufficient to avoid the need for cycling or running multiple columns in parallel. The inability to efficiently handle larger batches could negatively impact cost of goods and plant capacity. Additionally, the bioprocessing industry needs more convenient, cost effective tools in order to reduce cost of goods. Small, disposable purification technologies that can simultaneously reduce validation and labor costs are desirable. As the industry evolves, ion exchange membranes may become more advantageous for mAb processing.

Although column chromatography methods are robust and reliable, they generally have low mass throughput because separation performance is dependent on pore diffusion. Product and impurities must slowly diffuse into pores to access binding sites. By contrast, membranes are not pore diffusion limited. Separation performance is independent of flow rate and therefore membranes are capable of much higher mass throughputs compared to resins. Membranes are also more convenient than resins because they do not require column bodies, column packing/unpacking, or qualification. Industrial scale membranes are available in cartridge or self-encapsulated formats that can be disposed of after a single use, further eliminating validation costs associated with reuse and storage. Membranes are also smaller and significantly lighter than resin filled columns, which facilitates handling within a manufacturing facility.

Membranes do have some drawbacks. Compared to resins they are a relatively new technology that has yet to experience widespread integration at industrial-scale. The types of commercially available membranes and selection of well characterized ligands are limited. Membranes are also significantly more expensive than ion exchange resins. Additionally, they are not an optimum medium for performing industrial-scale bind and elute chromatography. Membranes have relatively low binding capacities which are difficult to economically offset through cycling. Many of these issues are likely to be resolved as new generations of membranes are developed.

Despite the drawbacks, membranes have established a niche in downstream purification. Ion exchange membranes have proven successful as a follow-up step to Protein A mAb capture. Membranes are ideal in this position because the impurity levels are low and, when used in flow-through mode, the binding capacity is no longer limiting. Flow-through chromatography is defined as a chromatographic operation where the target protein flows through the sorbent media without binding while appropriately charged impurities are adsorbed. Extended to membrane chromatography, it is a technique that capitalizes on a repulsive force established between the membrane and mAb so that the majority of binding sites remain available for the adsorption of oppositely charged CHOP species.

This study focuses on the purification of monoclonal antibodies using ion exchange membranes in indigenous protein displacement mode. The approach differs from flow-through because mAb is processed through the membrane at pH and conductivity conditions that cause product adsorption. This is accomplished by operating at low ionic strength and at a pH above the mAb pI during anion exchange, and below the mAb pI during cation exchange. At these conditions, an attractive force is established between membrane and mAb resulting in product adsorption. Feedstream loading continues beyond the breakthrough capacity and the membrane effluent is collected in a purified form. The experimental data for indigenous protein displacement mode show high purification and yield, which were not obvious given the strong electrostatic interaction between membrane and mAb.

Four recombinant DNA derived mAbs were selected for analysis based on their range of isoelectric points (pI 6.7-9.3, calculated based on amino acid sequence). All four mAbs were produced in CHO cell cultures at Genentech Inc. and were partially purified with one or more column chromatography steps (Protein A or Protein A & ion exchange). Feedstreams were chosen based on residual levels of Chinese hamster ovary protein (CHOP).

This study explores the ability of ion exchange membranes Mustang™ S, Mustang™ Q, and Sartobind™ S to clear CHOP at pH and conductivity conditions that also cause mAb adsorption. CHOP purification and yield were investigated as a function of pH, conductivity, load density, flow rate and membrane type. Membrane scale-up and regeneration were also studied, and the feasibility of continuous processing was explored.

Materials and Methods

Feedstream

The feedstreams were taken from industrial, pilot, or small-scale cell culture batches (Genentech Inc., South San Francisco, Calif.) initially produced for commercial or research purposes. Each feedstream was partially purified, meaning the cells were separated and the clarified fluid was purified over at least one column chromatography step (Protein A or Protein A & ion exchange). Each feedstream contained a target therapeutic monoclonal antibody (IgG1 or IgG4) and a quantifiable level of host cell impurities. The composition of each feedstream varied depending on the individual mAb process and the level of purification. In general, the feedstream pH was 5.5-8.0, conductivity was 3.2-9.0 mS/cm, and product concentration was 3.5-6.9 mg/mL. Table 1 shows feedstream characteristics for each of the mAbs used in this study.

mAb Quantification

The concentration of mAb was determined using UV-spectrophotometric scan at 280 and 320 nm. CHOP levels were too low to have an appreciably effect on UV absorbance. Samples containing mAb were diluted with appropriate non-interfering diluent into the range of 0.1 to 1.0 AU. Sample preparation and spec scan readings were performed in duplicate and the average value was recorded. The absorption coefficient for the mAbs tested was 1.45-1.70 $(mg/mL)^{-1}cm^{-1}$. The absorbance at 280 and 320 nm, dilution factor, path length (1 cm), and absorption coefficient were used to calculate the mAb concentration using the equation known as the Beer-Lambert Law, $$\text{Protein Concentration (mg/mL)} = \frac{A_{280} - A_{320}}{\text{abs.}coeff.} \times \text{dilution factor}$$

CHO Host Cell Proteins (CHOP) Quantification

An enzyme linked immunosorbent assay (ELISA) was used to quantitate the levels of CHOP. Affinity-purified goat anti-CHOP antibodies were immobilized on microtiter plate wells. Dilutions of the samples containing CHOP, standards, and controls, were incubated in the wells, followed by incubation with goat anti-CHOP antibodies conjugated to horseradish peroxidase. The horseradish peroxidase enzymatic activity was detected with o-phenylenediamine dihydrochloride. The CHOP was quantitated by reading absorbance at 492 nm in a microtiter plate reader. A computer curve-fitting program was used to generate the standard curve and automatically calculate the sample concentration. The assay range for the ELISA was typically 5 ng/ml to 320 ng/ml. For each sample, 2-4 dilutions were assayed and the values were averaged. CHOP values were divided by the mAb concentration and the results were reported in units of ppm (ng CHOP/mg mAb).

Filtrate samples exhibiting CHOP levels below the limit of quantification (LOQ) were subsequently concentrated to obtain quantifiable results. Samples were concentrated 10 fold using an Amicon® Ultra-15 centrifugal 10 kD MWCO filter (Millipore Corporation, Billerica, Mass.), and Eppendorf 5810R centrifuge (Eppendorf AG, Hamburg, Germany) at 5-25° C., and 3200-4000 rpm for 10-20 minutes.

Membranes

The membranes tested were the Mustang™ S and Q (Pall Corporation, East Hills, N.Y.) and Sartobind™ S (Sartorius-Stedim Biotech S.A., Aubagne, France). The Mustang™ S and Sartobind™ S are strong cation exchange membranes and the Mustang™ Q is a strong anion exchange membrane. The Mustang™ S and Sarlobind™ S are modified with a form of sulfonic acid and the Mustang™ Q is modified with a form of quaternary amine. The Mustang™ S and Q are made of polyethersulfone (PES) with 0.8 μm pores and the Sartobind™ S is made of regenerated cellulose with 3-5 μm pores. To increase binding capacity each manufacturer combines multiple layers of membrane into each device. The total number of layers and thickness vary depending on the manufacturer and the size of the device being fabricated. Membrane volume (MV) is the physical volume of the membrane (solids and voids) and is measured in units of mL. A variety of membrane devices representing multiple scales were used in this study. Table 2 lists the pertinent specifications for each membrane tested.

Filtration Systems

Small-scale tests were performed with an AKTA Explorer™ 100 (GE Healthcare, Fairfield, Conn.), which is a programmable process purification system that includes an integrated metering pump, pressure sensor, and in-line pH, conductivity, and UV sensor. The Explorer system was programmed and controlled through a computer running UNICORN™ v5.10 software (GE Healthcare, Fairfield, Conn.). Small-scale tests were also performed using a manual system consisting of a Masterflex® L/S® digital economy drive peristaltic pump (Cole Parmer, Vernon Hills, Ill.), in-line DTX™ Plus TNF-R pressure sensor (Becton Dickinson, Franklin Lakes, N.J.), and a AND EK-1200i balance (A&D Company, Ltd., Tokyo, Japan). The balance was used to physically monitor the flow rate of the pump by measuring mass accumulation. Mass was converted to volume assuming a feedstream density of 1.0 g/mL. The pressure from the in-line transducers and mass from the balance were continuously monitored using a NetDAQ™ 2640A/41A network data acquisition system (Fluke, Everett, Wash.) which was linked to a computer running Trendlink™ version 3.1.1 (Canary Labs Inc., Martinsburg, Pa.) and RsCom version 2.40 (A&D Company, Ltd., Tokyo, Japan) software for pressure and mass collection, respectively. Scale-up studies were performed using an AKTA Pilot™ (GE Healthcare, Fairfield, Conn.) running UNICORN™ v5.10 software. The Pilot was equipped with a larger pump but was functionally equivalent to the Explorer.

Filtrate Sample Collection Techniques

Filtrate was collected in three different ways. Grab samples and fractions were the most common. A grab sample is a small instantaneous aliquot of filtrate taken at a specific throughput. Fractions are larger filtrate samples and are defined by throughput ranges. Filtrate was also collected as a single large pool. Pool analysis is effective, but grab samples and fractions are generally more useful for monitoring mAb and CHOP levels because consecutive samples can be combined to show trends.

Experimental

Feedstock was removed from cold storage (2-8° C. or ≤−70° C.) and allowed to equilibrate to room temperature. It was then optionally pH and/or conductivity adjusted from the conditions shown in Table 1 using appropriate titrating agent (i.e. 1.5 M tris base or 1 M citric acid) or diluent (purified water or 5 M sodium chloride). It was then filtered offline using a 0.2 μm Millipak-20 (Millipore Corporation, Billerica, Mass.), AcroPak™ 20 (Pall Corporation, East Hills, N.Y.) or 1000 mL vacuum filter (Thermo Fisher Scientific, Rochester, N.Y.) to remove any precipitates that may have formed during cold storage or conditioning.

The filtration system was prepared by flushing the load and filtrate lines using purified water or appropriate buffer. The membrane was placed in-line downstream of the feed pump and pressure sensor and then it was flushed with 50-500 MV of purified water or equilibration buffer. After flushing, the feed was directed to the membrane and a variable amount was loaded at a constant flow rate of 333-2667 MV/hour. During the load phase the filtrate was sampled as necessary. The membrane was then optionally chased with buffer to collect any residual product. To maintain retention of impurities on the membrane, the chase (a.k.a wash buffer) buffer was generally similar in pH and equal to or lower in conductivity to the feed.

In some cases the membrane adsorber was eluted. Membrane elution was only performed using the Explorer or Pilot so that pooling could be facilitated by the in-line UV sensor. The membrane was eluted using a high salt buffer (20 mM sodium acetate and 350 mM sodium chloride, pH 5.5 or 25 mM his and 250 mM sodium chloride, pH 8.0) at a constant flow rate of 333-2667 MV/hour and was pooled from 0.5-0.5 OD.

Continuous Processing

Continuous processing experiments were performed on the AKTA Explorer. During these experiments the Q column flow-through was pH adjusted in-line and immediately loaded onto the Mustang™ S membrane. The Q column was packed with Q Sepharose Fast Flow resin (diameter×length: 1.1 cm×20 cm). The column outlet was attached to the inlet of a T-connection and pH adjustment was accomplished in-line by directing the "B Pump" to the opposite inlet of the T-connection. The T-connection provided adequate mixing and the pH adjusted solution was directed to the inlet of the Mustang™ S membrane. The flow rate through the column was maintained at 100 cm/hour (1.58 mL/min). The flow rate through the membrane was slightly higher (approximately 2.2%) due to the added fluid from the in-line pH adjustment.

Results

Small-Scale Cation Exchange (CEX) Membrane Performance

MAb 1 anion exchange pool at pH 5.5 and 6.0 mS/cm was processed over a small-scale 0.18 mL Mustang™ S membrane at a constant flow rate of 667 MV/hour. The mAb 1 pH was 3.4 pH units below the pI and therefore the antibody was positively charged. Feed and filtrate grab samples were analyzed for mAb and host cell impurities. FIG. 1 shows the Mustang™ S initially reduced CHOP from 38 to 4.3 ppm. CHOP rose slightly to 5.7 ppm as load density increased to 16,000 g/L. The results also show high yield was achieved, reaching approximately 100% after 5000 g/L.

To identify mAb and charge dependencies, mAb 2 anion exchange pool was processed over Mustang™ S at pH 5.5 and 8.0. The mAb 2 feedstream was split into equal portions, the first was maintained at pH 8.0 and 5.0 mS/cm, and the second was adjusted to pH 5.5 and 6.4 mS/cm using 1M citric acid. Both feedstreams were processed over a small-scale 0.18 mL Mustang™ S membrane at constant flow rate of 667 MV/hour. The mAb 2 at pH 5.5 and 8.0 was below the pI and therefore positively charged. Feed and filtrate grab samples were analyzed and the results for CHOP are shown in FIG. 2. At pH 5.5 the Mustang™ S initially reduced CHOP from 51 to 3.0 ppm, and similar to mAb 1, the levels increased with load density. Membrane performance decreased substantially at pH 8.0, clearly demonstrating that CHOP adsorption is pH dependent. FIG. 3 shows yield is similar at both pH conditions, and ≥96% is attainable after a load density of approximately 5000 g/L.

To evaluate adsorber performance on a cruder feedstream, mAb 1 Protein A pool at pH 5.5 and 3.2 mS/cm was processed over a small-scale 0.18 mL Mustang™ S membrane at a constant flow rate of 1333 MV/hour. The mAb 1 load was 3.4 units below the calculated pI and therefore the antibody was positively charged. Load, filtrate fractions, and elution samples were analyzed and the results for CHOP are shown in FIG. 4. The data show the Mustang™ S initially reduced CHOP from 438 to 109 ppm. CHOP increased to 318 ppm as load density approached 55,300 g/L. The membrane was eluted using a solution containing high salt. The salt ions are used to shield the charges, thus disrupting the electrostatic interactions and causing the proteins to desorb from the membrane surface and move freely into the mobile phase. Analysis of the elution pool shows an enrichment of impurities confirming that CHOP bind to the membrane due to electrostatic forces.

Small-Scale Anion Exchange (AEX) Membrane Performance

For comparison purposes MAb 3 was selected for testing using an anion exchange membrane above the isoelectric point of 7.7. Proteins are prone to deamidation and aggregation at high pH so similar tests were not performed on mAbs 1 and 2. Cation exchange pool at pH 5.5 and 9 mS/cm was pH adjusted to 8.0 using 1.5 M tris base. The feedstock was then split into three separate pools and conductivity was adjusted using purified water. The first pool was at 10 mS/cm, the second and third pools were adjusted to 7 mS/cm and 4 mS/cm, respectively. All three pools were maintained at pH 8.0. Each feedstream was then processed over a small-scale 0.35 mL Mustang™ Q at constant flow rate of 600 MV/hour. The mAb 3 at pH 8.0 was 0.3 pH units above the pI and therefore the antibody was negatively charged. Load and filtrate pools were analyzed and the results for CHOP are shown in FIG. 5. The data show that at 4 mS/cm the Mustang™ Q reduced CHOP from 180 to 0.6 ppm and that impurity clearance decreased at higher conductivities, presumably due to ionic shielding. FIG. 5 shows that although the pH was only 0.3 units above the pI, the charge on mAb 3 was strong enough to enable binding >10 mg/mL. Like CHOP clearance, mAb 3 binding also decreased at higher conductivities. FIG. 6 shows yield for mAb 3 increased rapidly, exceeding 96% after approximately 1000 g/L.

Process Combining AFX and CEX Membranes

MAb 4 was used to test the feasibility of employing consecutive indigenous protein displacement steps using both anion and cation exchange membranes. MAb 4 was desirable because its pI of 6.7 was low enough to enable processing at pH conditions both above and below the isoelectric point. Protein A pool at pH 5.0 and 3.5 mS/cm was adjusted to pH 8.0 and 4 mS/cm using 1.5 M tris base. The feedstock was then processed over a small-scale 0.18 mL Mustang™ Q membrane at a constant flow rate of 1333 MV/hour. The mAb 4 at pH 8.0 was 1.3 units above the pI and therefore the antibody was negatively charged. The Mustang™ Q filtrate fractions were sampled and then recombined and adjusted to pH 5.5 and 6.1 mS/cm using 1 M citric acid. The recombined pool was then processed over a small-scale 0.18 mL Mustang™ S membrane at a constant flow rate of 1333 MV/hour. The mAb 4 at pH 5.5 was 1.2 pH units below the pI and therefore the antibody was positively charged. Load and filtrate fractions were analyzed and the CHOP results for both membranes are shown in FIG. 7. The data show Mustang™ Q initially reduced CHOP from 1215 to 555 ppm, and the levels steadily increased to 726 ppm as load density approached 1700 g/L. The results also show that the CHOP decreased to 375 ppm after the recombined Mustang™ Q filtrate fractions were pH adjusted to 5.5. The exact cause of the decrease in CHOP is not known. The results for the subsequent testing using the Mustang™ S show that CHOP levels were further reduced to 143 ppm, and again steadily increased to approximately 168 ppm as load density approached 1500 g/L. Overall, the results demonstrate that it is feasible to combine membrane steps to further reduce host cell impurities.

A Continuous Process Combining Columns and Membranes

MAb 1 was used to test the feasibility of using column chromatography continuously and in series with ion exchange membranes run in indigenous protein displacement mode. Two runs were performed. During Run 1 the column and membrane were analyzed separately (batch mode) and during Run 2 the column and membrane were run simultaneously in series (continuous mode). The batch operations for Run 1 are as follows. Conditioned mAb 1 Protein A pool (pH 8.0 and 4.7 mS/cm) was loaded onto a Q Sepharose Fast Flow column. The pH of the Q Seph FF load was 0.9 pH units below the pI so the antibody was positively charged, resulting in a repulsive force between resin and mAb. The mode of operation can be characterized as traditional flow-through column chromatography. Flow-through grab samples were collected throughout the run. The column was loaded to approximately 136 g/L resin. The Q Seph FF pool was collected and pH adjusted to 5.5 and 6 mS/cm using 1 M citric acid. It was then processed over a small-scale 0.18 mL Mustang™ S membrane at 538 MV/hour to a load density of approximately 15,000 g/L membrane. The pH of the membrane load was approximately 3.4 units below the calculated pI and therefore the antibody was positively charged. Membrane effluent grab samples were collected throughout the run. The used Mustang™ S membrane was discarded and the Q Seph FF column was regenerated using 0.5M NaOH and then stored in 0.1N NaOH. Run 2 was performed in a similar manner to Run 1; however, the Q Seph FF flow-through was pH adjusted in-line and then immediately loaded onto the Mustang™ S membrane. Load and column/membrane grab samples were analyzed and the CHOP results are summarized for batch (Run 1) and continuous (Run 2) experiments in FIG. 8. The data show that CHOP in the Protein A pool were reduced from 1450 ppm to approximately 16.8 ppm over the Q Sepharose column. It should be noted that the Q pool value of 16.8 ppm was calculated based on the grab sample results taken throughout the run. The batch and continuous Mustang™ S results (12.7 and 11.1 ppm) show good agreement. Overall, the data demonstrate that linking column and membrane steps into a single continuous process is feasible and produces results comparable to traditional batch operations.

Comparison Between Membrane Manufacturers

Sartobind™ S membrane was tested using mAb 1 to compare performance between membrane suppliers. mAb 1 anion exchange pool at pH 5.5 and 6 mS/cm was processed over a small-scale 0.14 mL Sartobind™ S membrane at a constant flow rate of 857 MV/hour. The mAb 1 load pH was 3.4 pH units below the pI and therefore the antibody was positively charged. Feed and filtrate fractions were analyzed for CHOP and the results are shown in FIG. 9. The data show the Sartobind™ S initially reduced CHOP from 29 to 3.3 ppm, and after approximately 11,500 g/L the levels increased slightly to 5.6 ppm. The data demonstrate that the Sartobind™ S and Mustang™ S membranes have similar CHOP adsorption.

Flow Rate Effect

Mustang™ S CHOP clearance was studied at 333-2667 MV/hour to test the impact of flow rate. MAb 1 anion exchange pool at pH 5.5 and 6 mS/cm was processed over four separate small-scale 0.18 mL Mustang™ S membranes from the same device lot. The mAb 1 load was 3.4 pH units below the pI and therefore the antibody was positively charged. Feed and filtrate grab samples were analyzed for CHOP and the results are shown in FIG. 10. The data show the Mustang™ S initially reduced CHOP from 45 to approximately 6.9 ppm. After 16,000 g/L the CHOP increased to average of 8.7 ppm. As expected for a membrane device not subject to the limitations of pore diffusion, the results show CHOP adsorption is independent of flow rate.

Scale-Up

A pilot-scale Mustang™ S membrane was used to verify CHOP clearance and yield upon scale-up. A 10 mL 16 layer device was selected because it was the smallest fully representative device available. It was considered fully representative because the number of membrane layers, pleating, and device assembly were similar to much larger industrial-scale capsules. The 10 mL device represented a 55 fold increase in scale from the previously studied small-scale device. MAb 1 anion exchange pool at pH 5.5 and 6 mS/cm was processed over the pilot-scale adsorber using the AKTA Pilot™. The mAb 1 load was 3.4 pH units below the pI and therefore the antibody was positively charged. To gain a sense of reproducibility the mAb 1 load was tested on the same 10 mL device two times. Between cycles the membrane was eluted with a high salt buffer (20 mM sodium acetate, 350 mM sodium chloride, pH 5.5) and regenerated using 0.5 M NaOH. The flow rate for all phases was 546 MV/hour. Feed and filtrate grab samples and elution pool were analyzed for CHOP and the results are shown in FIG. 11. The data show good reproducibility between cycles, indicating the Mustang™ S can be regenerated at least once. Analysis of the elution sample showed enrichment of impurities, confirming for a second time that CHOP bind to the membrane due to electrostatic forces. A comparison to previous small-scale results for mAb 1 shows good agreement for CHOP and yield. The data demonstrate that small-scale devices are capable of predicting large-scale performance.

Conclusion

Ion exchange membranes were shown to be effective at removing CHOP in a mode similar to flow-through mode chromatography but at pH and conductivity conditions that cause mAb binding. The technique has been called indigenous protein displacement ion exchange membrane chromatography. Results have demonstrated that this technique can be used to clear CHOP without substantial yield loss that would likely occur with a traditional resin filled column sized in order to maintain yield, purity, and process time. The data have shown that mAbs having previously undergone partial purification using Protein A and ion exchange column chromatography can be further purified to CHOP levels less than 10 ppm with yields ≥96% using Mustang™ S, Sartobind™ S, and Mustang™ Q. Low CHOP levels were maintained at high load densities, and in some instances, performance was maintained to 16,000 g/L. Results have shown that impurity clearance is dependent on load pH, and in general, decreases with higher conductivity. Additionally, feasibility studies demonstrated that multiple membranes can be used in combination to further reduce impurity levels and that column, and membrane steps can be integrated into a single continuous purification process. A comparison between Mustang™ S and Sartobind™ S showed similar impurity clearance. Although there are notable differences in the membranes, results were similar and therefore the mechanism of impurity removal is not membrane dependent. Test results at flow rates ranging from 333-2667 MV/hour were consistent with theory and literature claims that membrane performance is independent of flow rate. Finally, experimentation with an intermediate device representing a 55 fold increase in scale showed similar performance to a small-scale membrane. The data confirm that small-scale devices are capable of predicting performance at production-scale. Additionally, sodium chloride followed by sodium hydroxide cleaning of the pilot-scale device between duplicate runs showed that membrane adsorbers can be regenerated and used more than once without a decline in performance.

The need for better purification technologies is clear. Increasing bioreactor titers may overburden column based purification platforms, and the challenge may not be met by solely increasing resin binding capacity. Additionally, to lower cost of goods the industry needs more convenient, cost effective tools. Membrane adsorbers are small and disposable and can reduce validation and labor costs while increasing mass throughput. Experimental results for ion exchange membranes operated in indigenous protein displacement mode showed high impurity clearance and yield, making this technique an attractive option for bioprocessing.

TABLE 1

Feedstream characteristics.

| Product | Upstream Process | Nomenclature | pH | Cond. mS/cm | Conc. g/L | IgG type | pI [b] |
|---|---|---|---|---|---|---|---|
| mAb 1 | Protein A [a] | Protein A Pool | 5.5 | 3.2 | 5.9-6.9 | 1 | 8.9 |
| mAb 1 | Protein A followed by Anion Exchange Flow-Through [a] | Anion Exchange Pool | 5.5 | 6.0 | 4.8 | 1 | 8.9 |
| mAb 2 | Protein A followed by Anion Exchange Flow-Through | Anion Exchange Pool | 8.0 | 5.0 | 5.4 | 1 | 9.3 |
| mAb 3 | Protein A followed by Cation Exchange Bind/Elute | Cation Exchange Pool | 5.5 | 9.0 | 4.1 | 1 | 7.7 |
| mAb 4 | Protein A Pool [a] | Protein A Pool | 5.0 | 3.5 | 3.2 | 4 | 6.7 |

Feedstock samples were collected from industrial, pilot, and small-scale processes.
[a] Pool pH and conductivity have been previously adjusted to ensure adequate product stability.
[b] The isoelectric point (pI) was calculated based on the amino acid sequence for each mAb.

TABLE 2

Membrane characteristics.

| Membrane | Device | Part No. | Layers No. | Membrane Volume (MV) mL | Pore Size μm |
|---|---|---|---|---|---|
| Mustang™ S | 25 mm Acrodisc® | MSTG25S6 | 6 | 0.18 | 0.8 |
| Mustang™ S | Capsule | CLM05MSTGSP1 | 16 | 10 | 0.8 |
| Sartobind™ S | 25 mm MA5 | S5F | 1 | 0.14 | 3-5 |
| Mustang™ Q | Coin | MSTG18Q16 | 16 | 0.18 | 0.8 |
| Mustang™ Q | 25 mm Acrodisc® | MSTG25Q6 | 6 | 0.35 | 0.8 |

What is claimed is:

1. A method for purifying a recombinant monoclonal antibody from a Chinese Hamster Ovary (CHO) cell culture composition comprising the antibody and Chinese hamster ovary protein (CHOP), which method comprises the sequential steps of:
   a. subjecting the composition to cation exchange chromatography performed in indigenous protein displacement mode, comprising feedstream loading the composition on a cation exchange membrane, wherein the antibody and the membrane have opposite charge as a result of the loaded composition having a pH of 1 to 5 pH units below the pI of the antibody and a conductivity of <40 mS/cm, which prevents the shielding of charges by buffer ions and cause the membrane to bind both the antibody and CHOP,
   b. continuing to load the membrane beyond the breakthrough capacity to a load density of at least 2000 g/L, wherein the bound antibody is displaced from the membrane by the binding of CHOP, and
   c. recovering the purified antibody from the effluent.

2. The method of claim 1 wherein the cation exchange membrane has a pore size of 0.1 to 100 μm.

3. The method of claim 1 wherein the pH is 1 to 4 pH units below the pI of the antibody.

4. The method of claim 1 wherein the pH is 1 to 3 pH units below the pI of the antibody.

5. The method of claim 1 wherein the pH is 1 to 2 pH units below the pI of the antibody.

6. The method of claim 1 wherein the pH is 1 pH unit below the pI of the antibody.

7. The method of claim 1 wherein the conductivity is ≤20 mS/cm.

8. The method of claim 1 wherein the conductivity is ≤10 mS/cm.

9. The method of claim 1, wherein the CHOP is reduced about 4-fold to about 17-fold from the recombinant antibody.

10. The method of claim 1, wherein the load density ranges from 2,000 g/L to 16,000 g/L.

11. The method of claim 1, wherein the pI of the antibody is greater than 8.

12. The method of claim 1, wherein the antibody is bevacizumab.

13. A method for purifying a recombinant monoclonal antibody from a Chinese Hamster Ovary (CHO) cell culture composition comprising the antibody and Chinese hamster ovary protein (CHOP), which method comprises the sequential steps of:
   a. subjecting the composition to anion exchange chromatography performed in indigenous protein displacement mode, comprising feedstream loading the composition on an anion exchange membrane, wherein the antibody and the membrane have opposite charge, as a result of the loaded composition having a pH of 1 to 5 pH units above the pI of the antibody and a conductivity of <40 mS/cm, which prevents the shielding of charges by buffer ions and cause the membrane to bind both the antibody and CHOP,
   b. continuing to load the membrane beyond the breakthrough capacity to a load density of at least 1000 g/L, wherein the bound antibody is displaced from the membrane by the binding of CHOP, and
   c. recovering the purified antibody from the effluent.

14. The method of claim 13 wherein the pH is 1 to 4 pH units above the pI of the antibody.

15. The method of claim 13 wherein the pH is 1 to 3 pH units above the pI of the antibody.

16. The method of claim 13 wherein the pH is 1 to 2 pH units above the pI of the antibody.

17. The method of claim 13 wherein the pH is 1 pH unit above the pI of the antibody.

18. The method of claim 13 wherein the conductivity is ≤20 mS/cm.

19. The method of claim 13 wherein the conductivity is ≤10 mS/cm.

20. The method of claim 13, wherein the CHOP is reduced about 300-fold from the recombinant antibody.

21. The method of claim 1 or 13, wherein the membrane is a mixed mode adsorber.

22. The method of claim 1 or 13, wherein the antibody is a monoclonal antibody.

23. The method of claim 1 or 13, further comprising subjecting the composition comprising the antibody to one or more further purification step(s) either before, during, or after steps a through b, said purification step being protein A affinity chromatography.

24. The method of claim 1 or 13, further comprising subjecting the composition comprising the antibody to one or more further purification step(s) either before, during, or after steps a through b, said purification step being ion exchange chromatography.

25. The method of claim 1 or 13, further comprising subjecting the composition comprising the antibody to one or more further purification step(s) run continuously during steps a through b, said purification step being ion exchange chromatography.

26. The method of claim 1 or 13, further comprising preparing a pharmaceutical composition by combining the purified antibody with a pharmaceutically acceptable carrier.

27. The method of claim 1 or 13, wherein the antibody yield is ≥96%.

28. The method of claim 1 or 13, wherein the CHOP is reduced about 4-fold to about 300-fold from the recombinant antibody.

29. The method of claim 1 or 13, wherein the purified antibody contains less than 10 ppm CHOP.

* * * * *